United States Patent … US 11,059,014 B2
Nakajima et al. … Date of Patent: Jul. 13, 2021

(54) NANOCLUSTER LIQUID DISPERSION, NANOCLUSTER FILM, NANOCLUSTER SOLID DISPERSION, METHOD FOR PRODUCING NANOCLUSTER LIQUID DISPERSION, AND DEVICE FOR PRODUCING NANOCLUSTER LIQUID DISPERSION

(71) Applicants: JAPAN SCIENCE AND TECHNOLOGY AGENCY, Kawaguchi (JP); AYABO CORPORATION, Anjo (JP)

(72) Inventors: Atsushi Nakajima, Kawasaki (JP); Hironori Tsunoyama, Kawasaki (JP); Hiroki Akatsuka, Tokyo (JP); Keizo Tsukamoto, Anjo (JP)

(73) Assignees: JAPAN SCIENCE AND TECHNOLOGY AGENCY, Kawaguchi (JP); AYABO CORPORATION, Anjo (JP)

( * ) Notice: Subject to any disclaimer, the term of this patent is extended or adjusted under 35 U.S.C. 154(b) by 347 days.

(21) Appl. No.: 15/752,986

(22) PCT Filed: Aug. 12, 2016

(86) PCT No.: PCT/JP2016/073737
§ 371 (c)(1),
(2) Date: May 18, 2018

(87) PCT Pub. No.: WO2017/030087
PCT Pub. Date: Feb. 23, 2017

(65) Prior Publication Data
US 2018/0361340 A1 Dec. 20, 2018

(30) Foreign Application Priority Data
Aug. 17, 2015 (JP) ............................. JP2015-160680

(51) Int. Cl.
*B01J 13/00* (2006.01)
*C23C 14/00* (2006.01)
(Continued)

(52) U.S. Cl.
CPC ........... *B01J 13/0043* (2013.01); *B01J 13/00* (2013.01); *B01J 13/0026* (2013.01);
(Continued)

(58) Field of Classification Search
CPC .... B01J 13/0043; B01J 13/00; B01J 13/0026; B22F 1/0022; B22F 9/24; B82Y 30/00; B82Y 40/00
See application file for complete search history.

(56) References Cited

U.S. PATENT DOCUMENTS 5,759,634 A 6/1998 Zang
6,494,932 B1 12/2002 Abercrombie
(Continued)

FOREIGN PATENT DOCUMENTS

EP 2 204 349 A1 7/2010
JP 2004-52068 A 2/2004
(Continued)

OTHER PUBLICATIONS

English-language machine translation of JP-2008266745-A, conducted on Espacenet May 7, 2020.*
(Continued)

*Primary Examiner* — Nicholas E Hill
(74) *Attorney, Agent, or Firm* — Oblon, McClelland, Maier & Neustadt, L.L.P.

(57) ABSTRACT

The present invention relates to a nanocluster liquid dispersion where nanoclusters with a predetermined number of atoms are dispersed.

6 Claims, 10 Drawing Sheets

(51) Int. Cl.
  *B82Y 5/00* (2011.01)
  *C23C 14/34* (2006.01)
  *B22F 1/00* (2006.01)
  *B22F 9/24* (2006.01)
  *B82Y 30/00* (2011.01)
  *B82Y 40/00* (2011.01)

(52) U.S. Cl.
  CPC .............. *B22F 1/0022* (2013.01); *B22F 9/24* (2013.01); *B82Y 5/00* (2013.01); *C23C 14/00* (2013.01); *C23C 14/34* (2013.01); *B82Y 30/00* (2013.01); *B82Y 40/00* (2013.01)

(56) References Cited

U.S. PATENT DOCUMENTS

| | | |
|---|---|---|
| 2003/0017106 A1 | 1/2003 | Abercrombie |
| 2005/0087037 A1 | 4/2005 | Abercrombie |
| 2006/0222790 A1 | 10/2006 | Roop |
| 2007/0052516 A1 | 3/2007 | Hines et al. |
| 2007/0172653 A1 | 7/2007 | Berkland et al. |
| 2009/0053316 A1 | 2/2009 | Berkland et al. |
| 2009/0081295 A1 | 3/2009 | Berkland et al. |
| 2010/0167078 A1 | 7/2010 | Kim et al. |
| 2012/0230913 A1 | 9/2012 | Johnston et al. |
| 2013/0099152 A1 | 4/2013 | Lee et al. |
| 2016/0091445 A1 | 3/2016 | Ayesh |

FOREIGN PATENT DOCUMENTS

| | | |
|---|---|---|
| JP | 2005-39103 A | 2/2005 |
| JP | 2006-316237 A | 11/2006 |
| JP | 2007-231306 A | 9/2007 |
| JP | 2008-266745 A | 11/2008 |
| JP | 2008266745 A * | 11/2008 |
| JP | 2009-117797 A | 5/2009 |
| JP | 2009-246213 A | 10/2009 |
| JP | 2009246213 A * | 10/2009 |
| JP | 2012-158785 A | 8/2012 |
| JP | 5493139 B1 | 3/2014 |
| WO | WO 01/94650 A2 | 12/2001 |
| WO | WO 2007/076295 A2 | 7/2007 |
| WO | WO 2014/199287 A1 | 12/2014 |

OTHER PUBLICATIONS

English-language machine translation of JP-2JP-2009246213-A, conducted on Espacenet May 7, 2020.*
C. H. Zhang et al., "Development of Cluster ion Source Based on Modulated Pulse Power Magnetron Sputtering Technique," The 8th Annual IEEE International Conference on Nano/Micro Engineered and Molecular Systems 428 (2013).*
Extended European Search Report dated Aug. 23, 2019 in Patent Application No. 16837077.3, citing documents AA—AE, AO, AP and AW-AY therein, 16 pages.
A. Pillonnet, et al., "Rare-Earth-Based Nanoclusters Embedded in Sol-Gel Waveguiding Thin Films", Journal of Luminescence, Elsevier, vol. 119-120, XP028045333, Jul. 1, 2006, pp. 560-564.
Fahrettin Yakuphanoglu, "Nanocluster n—CdO Thin Film by Sol-Gel for Solar Cell Applications", Applied Surface Science, Elsevier, vol. 257, No. 5, XP027431529, Dec. 15, 2010 pp. 1413-1419.
Minyung Lee, et al, "Microstructure and Surface Plasmon Absorption of Sol-Gel-Prepared Au Nanoclusters in $TiO_2$ Thin Films", Nanostructured Materials, Elsevier. vol. 11, No. 2, XP004175488, Mar. 1, 1999, pp. 195-201.
Partial Supplementary European Search Report dated Jul. 15, 2019, in Patent Application No. 16837077.3, citing documents AA-AH, AO-AP and AX therein, 14 pages.
Stepanov, A. et al., "Water transverse relaxation rates in aqueous dispersions of superparamagnetic iron oxide nanoclusters with diverse hydrophilic coating", Colloids and Surfaces A: Physiochemical and Engineering Aspects, XP028814776, vol. 443, Dec. 16, 2013, pp. 450-458.
International Search Report dated Nov. 15, 2016 in PCT/JP2016/073737 (with English translation), citing documents AP-AU therein, 4 pages.
Yoshikiyo Hatakeyama, et al., "Synthesis of Au Nanoparticles by Sputter Deposition onto Polyethyleno Glycol: Effects of Preparation Temperature and Added Substances" Bulletin of Society of Nano Science and Technology, vol. 10, No. 1, 2011, pp. 27-33 (with English Abstract).
M. Wagener, et al., "High Pressure DC-Magnetron Sputtering on Liquids: A new Process for the Production of Metal Nanosuspensions" Progr. Colloid Polym. Sci., vol. 111, 1998, pp. 78-81.
Yujin Hwang, et al., "Production and Dispersion Stability of Nanoparticles in Nanofluids" Powder Technology, Elsevier, vol. 186, 2008, pp. 145-153.

* cited by examiner

NANOCLUSTER LIQUID DISPERSION, NANOCLUSTER FILM, NANOCLUSTER SOLID DISPERSION, METHOD FOR PRODUCING NANOCLUSTER LIQUID DISPERSION, AND DEVICE FOR PRODUCING NANOCLUSTER LIQUID DISPERSION

TECHNICAL FIELD

The present invention relates to a nanocluster liquid dispersion, a nanocluster film, a nanocluster solid dispersion, a method for producing a nanocluster liquid dispersion and a device for producing a nanocluster liquid dispersion.

BACKGROUND ART

Nanoclusters are ultrafine particles in which several to several thousands of atoms or molecules are collected. Nanoclusters are larger than atoms and smaller than bulk solids and have a particle diameter of about 0.2 to 8 nm. Nanoclusters have unique properties and functions and are expected to be able to be applied to various applications such as catalysts, optoelectronic devices, magnetic devices, biosensors, probes, and diagnostic agents (indicators).

Nanoclusters are generated by various methods.

For example, Patent Document 1 and 2, and Non Patent Document 1 to 3 describe that nanoclusters are generated by neutral atoms or atomic ions generated by a magnetron sputtering method being injected into a liquid phase, and atoms aggregating on a surface of or in the liquid phase.

Patent Document 3 discloses a method of aggregating neutral atoms or atomic ions generated by a magnetron sputtering method in a gas phase. According to aggregation in the gas phase, a distribution of the number of atoms constituting a nanocluster (hereinafter referred to as a cluster size) is controlled.

CITATION LIST

Patent Document

[Patent Document 1]

Japanese Unexamined Patent Application, First Publication No. 2007-231306

[Patent Document 2]

Japanese Unexamined Patent Application, First Publication No. 2012-158785

[Patent Document 3]

Japanese Patent No. 5493139

Non Patent Document

[Non Patent Document 1]

Hatakeyama Yoshikiyo, Kato Junichi, Ohnishi Kei, Nishikawa Keiko; Nano Society Proceedings, Vol, 10, No. 1.

[Non Patent Document 2]

M. Wagener et al., Progr Colloid Polym Sci, 1998, 111, 78-81.

[Non Patent Document 3]

Yujin Hwang et al., Powder Technology, 186 (2008) 145-153.

SUMMARY OF INVENTION

Technical Problem

The properties of nanoclusters may change greatly with an increase or decrease of a single atom. Therefore, it is required to efficiently obtain nanoclusters having uniform cluster sizes.

However, in the methods described in Patent Document 1 and 2, and Non Patent Document 1 to 3, neutral atoms or atomic ions aggregate on the surface of or in a liquid phase. Thus, neutral atoms or atomic ions that self-aggregate need to be elements that have a low ionization tendency (are easily reduced) and easily aggregate. When neutral atoms or atomic ions that self-aggregate are not elements that easily aggregate, it is not possible to generate nanoclusters.

In addition, in the methods described in Patent Document 1 and 2, and Non Patent Document 1 to 3, when the temperatures, stirring conditions, amounts of additives, and the like are changed, the nanocluster size distributions become wider. That is, it is not possible to efficiently obtain nanoclusters with uniform cluster sizes.

In the method described in Patent Document 3, fine particles were generated by aggregating neutral atoms and atomic ions in a gas phase. For this reason, unlike Patent Document 1 and 2, and Non Patent Document 1 to 3, types of atoms (elements) for generating nanoclusters are not limited. In addition, the nanoclusters obtained by the method described in Patent Document 3 have uniform cluster sizes. However, when nanoclusters in a gas phase are collected, they are deposited on a solid substrate. When nanoclusters are deposited on a solid substrate, the nanoclusters may aggregate and combine with each other on the substrate. In addition, it is extremely difficult to peel off the nanoclusters and collect them from the solid substrate. That is, while it is possible to generate nanoclusters whose cluster sizes are controlled, it is difficult to efficiently collect the nanoclusters.

An object of the present invention is to provide a nanocluster liquid dispersion in which nanoclusters with a predetermined number of atoms (clusters with a controlled cluster size) are dispersed, a nanocluster solid dispersion and a nanocluster dispersion film. In addition, an object of the present invention is to provide a method for producing a nanocluster liquid dispersion through which it is possible to efficiently collect nanoclusters and a production device.

Solution to Problem

The inventors postulated that nanoclusters could be collected three-dimensionally using a liquid phase to increase a yield of the nanoclusters. Thus, the inventors found that, when nanoclusters with a predetermined cluster size are generated and the generated nanoclusters are collected in a dispersion medium, it is possible to efficiently collect nanoclusters whose cluster sizes are controlled.

That is, in order to solve the above problem, the following aspects are used.

(1) In a nanocluster liquid dispersion according to a first aspect, nanoclusters with a predetermined number of atoms are dispersed.

(2) In the nanocluster liquid dispersion according to the above aspect, nanoclusters with a predetermined number of atoms may be uniformly dispersed.

(3) In the nanocluster liquid dispersion according to the above aspect, a dispersion medium in which the nanoclusters are dispersed may be a solvent having low volatility.

(4) In the nanocluster liquid dispersion according to the above aspect, the dispersion medium may have an ether bond or a siloxane bond.

(5) In the nanocluster liquid dispersion according to the above aspect, an end of the ether bond or the siloxane bond may have an inert substituent terminal.

(6) In the nanocluster liquid dispersion according to the above aspect, a dispersion medium in which the nanoclusters are dispersed may be a volatile solvent.

(7) In the nanocluster liquid dispersion according to the above aspect, the dispersion medium may be any one selected from the group consisting of acyclic ethers, cyclic ethers, acyclic siloxanes, nitriles, haloalkanes, alcohols, amides, sulfoxides, and benzene derivatives.

(8) In the nanocluster liquid dispersion according to the above aspect, a constituent unit of the nanocluster may be a metal element or a main group element whose ionization tendency is higher than Ag, or a complex thereof.

(9) In the nanocluster liquid dispersion according to the above aspect, the nanocluster may be a metal-ion-encapsulating silicon cage cluster represented by M@Si.

(10) In the nanocluster liquid dispersion according to the above aspect, the nanocluster may be any one selected from the group consisting of a binary cluster of Ta and Si, a binary cluster of Ti and Si, a binary cluster of Lu and Si, a binary cluster of Mo and Si, a binary cluster of W and Si, and a binary cluster of Ru and Si.

(11) In the nanocluster liquid dispersion according to the above aspect, a proportion of the nanoclusters with a predetermined number of atoms with respect to nanoclusters included in the nanocluster liquid dispersion may be 5% or more.

(12) A nanocluster solid dispersion according to an aspect of the present invention includes nanoclusters with a predetermined number of atoms.

(13) A nanocluster film according to an aspect of the present invention includes nanoclusters with a predetermined number of atoms

(14) A method for producing a nanocluster liquid dispersion according to a second aspect includes generating nanoclusters and collecting the nanoclusters in a dispersion medium while flowing the dispersion medium on which the generated nanoclusters are incident.

(15) In the method for producing a nanocluster liquid dispersion according to the above aspect, the dispersion medium may flow so that a density of nanoclusters on the surface of the dispersion medium may not exceed an aggregation limit in the collecting.

(16) In the method for producing a nanocluster liquid dispersion according to the above aspect, the dispersion medium may be a solvent having low volatility with a boiling point of 160° C. or more and a vapor pressure of 100 Pa or less at room temperature.

(17) In the method for producing a nanocluster liquid dispersion according to the above aspect, after the collecting, replacing the dispersion medium with a volatile dispersion medium having a lower boiling point than the dispersion medium may be additionally included.

(18) In the method for producing a nanocluster liquid dispersion according to the above aspect, detecting whether predetermined nanoclusters are generated in the generating may be additionally included between the generating and the collecting.

(19) A device for producing a nanocluster liquid dispersion according to a third aspect includes a nanocluster generation unit; and a nanocluster collection unit that is arranged in a traveling direction of nanoclusters generated in the nanocluster generation unit.

(20) In the device for producing a nanocluster liquid dispersion according to the above aspect, the nanocluster generation unit may include a vacuum chamber, a sputtering source including a target as a cathode and configured to perform magnetron sputtering and generate a plasma, a pulse power supply configured to supply power to the sputtering source, a first inert gas supply unit configured to supply a first inert gas to the sputtering source, and a nanocluster growth cell that is housed in the vacuum chamber.

(21) In the device for producing a nanocluster liquid dispersion according to the above aspect, the nanocluster collection unit may include a storage chamber in which a dispersion medium is able to be stored and a flowing unit that is able to flow the dispersion medium on a surface on which the nanoclusters are incident.

(22) In the device for producing a nanocluster liquid dispersion according to the above aspect, the flowing unit may be a stirring bar that is provided in the storage chamber.

(23) In the device for producing a nanocluster liquid dispersion according to the above aspect, the flowing unit may be a rotating body having an axis of rotation in a direction perpendicular to a direction in which the nanoclusters travel, and the rotating body may be arranged so that a part thereof is immersed in the dispersion medium stored in the storage chamber.

(24) In the device for producing a nanocluster liquid dispersion according to the above aspect, the nanocluster collection unit may include a substrate that intersects the traveling direction of the nanocluster, a cooling mechanism configured to cool the substrate, a dispersion medium supply unit configured to spray a dispersion medium onto the substrate, and a collection container that is provided below the substrate.

(25) In the device for producing a nanocluster liquid dispersion according to the above aspect, a detection unit configured to detect the nanoclusters may be additionally included between the nanocluster generation unit and the nanocluster collection unit.

Advantageous Effects of Invention

In a nanocluster liquid dispersion according to an aspect of the present invention, nanoclusters with a controlled cluster size (number of atoms) are dispersed. Thus, it is possible to prepare a nanocluster film by an existing method such as coating.

In a nanocluster film according to an aspect of the present invention, a cluster size is controlled and functions unique to nanoclusters can be exhibited. Thus, it can be appropriately used for various applications, for example, catalysts, electronic devices, magnetic devices, biosensors, probes, and diagnostic agents (indicators).

In a method for producing a nanocluster liquid dispersion according to an aspect of the present invention, it is possible to efficiently collect nanoclusters without aggregating in the liquid dispersion.

In a device for producing a nanocluster liquid dispersion according to an aspect of the present invention, it is possible to efficiently collect nanoclusters.

BRIEF DESCRIPTION OF DRAWINGS

FIG. 9A shows the entire image of the mass spectrum, and FIG. 9B is an enlarged view in which the peak part is enlarged.

DESCRIPTION OF EMBODIMENTS

Figure 1:
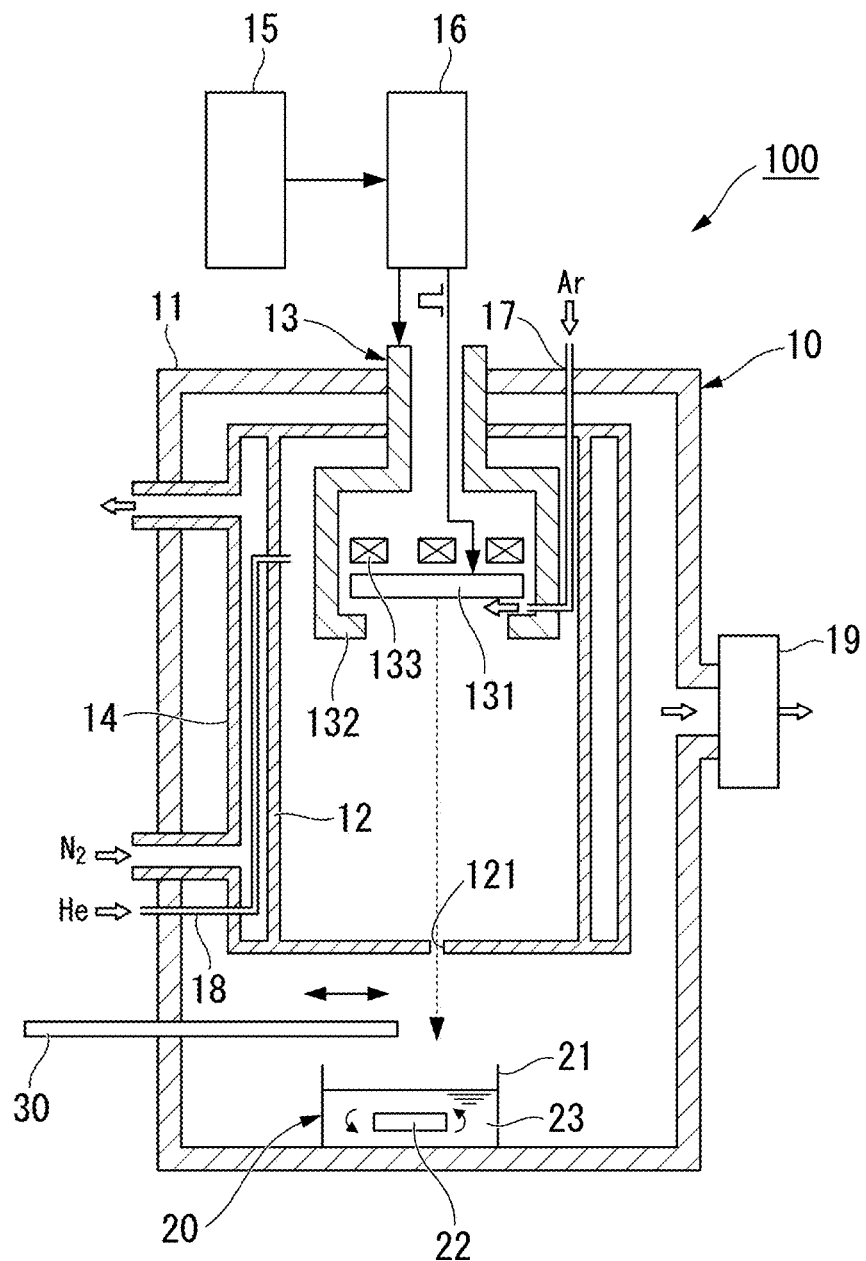
FIG. 1 is a schematic cross-sectional view of a device for producing a nanocluster liquid dispersion according to a first embodiment.

Configurations of the present invention will be described below with reference to the drawings as necessary. In the drawings used in the following description, in order to facilitate understanding of features, characteristic parts are enlarged for convenience of illustration in some cases, and dimensional ratios between components may not be the same as actual ones. The exemplified materials, dimensions, and the like are only examples, and the present invention is not limited thereto and can be appropriately changed and implemented within a range not changing the scope and spirit of the invention.

Nanocluster Liquid Dispersion

A nanocluster liquid dispersion according to an aspect of the present invention includes nanoclusters and a dispersion medium. The nanoclusters mainly include a nanocluster with a predetermined number of atoms (cluster size). Here, "mainly" means that, when the horizontal axis represents the number of atoms in the nanocluster and the vertical axis represents the number of nanoclusters (signal strength), a peak can be observed. The number of atoms in which a peak occurs is a predetermined number of atoms. The number of peaks generated is not limited to one.

Nanoclusters are dispersed in the dispersion medium without aggregating, and preferably uniformly dispersed.

Here, "dispersion" means that no precipitation, which is nanocluster aggregates in a macro-perspective, is observed visually. In addition, "uniform dispersion" means that no precipitation, which is nanocluster aggregates in a macro-perspective, is observed visually, and nanoclusters are not associated with each other in a micro-perspective.

Here, "not associated" means that, among nanoclusters in a dispersion medium immediately after dispersion, 60% or more of the nanoclusters are not associated with each other after one day. In addition, among nanoclusters in a dispersion medium immediately after dispersion, preferably, 80% or more of the nanoclusters are not associated with each other after one day and more preferably, 90% or more of the nanoclusters are not associated with each other after one day. In addition, preferably, nanoclusters are not associated with each other even after 1 week.

Among nanoclusters in a dispersion medium immediately after dispersion, a proportion of the associated nanoclusters can be measured by the following procedure.

First, nanoclusters are dispersed in a dispersion medium. Then, immediately after dispersion (within 1 hour), part thereof is extracted, and a particle size distribution is measured through chromatography or the like. Then, the same operation is performed after one day. The obtained particle size distribution immediately after dispersion and the obtained particle size distribution after one day are compared. At this time, in the particle size distribution after one day, when a peak occurs in part of an integer multiple of the main peak in the particle size distribution immediately after dispersion, it is said that they are associated. Since association means that nanoclusters are bonded to each other, an apparent size of nanoclusters after association is an integer multiple of nanoclusters before association.

When it is confirmed that association has occurred, a proportion of the associated nanoclusters is calculated. First, nanoclusters with a predetermined cluster size that are most abundant in the liquid dispersion immediately after dispersion are identified. Then, an area (first area) occupied by the identified nanoclusters with a predetermined cluster size in a dispersion curve of the particle size distribution immediately after dispersion is calculated. Next, an area (second area) occupied by the identified nanoclusters with a predetermined cluster size in a dispersion curve of the particle size distribution after one day is calculated. When predetermined nanoclusters are associated with each other, the second area is smaller than the first area. A change in the area is caused by a decrease in the number of nanoclusters with a predetermined cluster size due to association. That is, when a ratio of the second area with respect to the first area is determined, a proportion of the associated nanocluster is calculated.

Here, while details will be described below, in a nanocluster liquid dispersion according to an aspect of the present invention, in principle, a reaction of $M_n + M \rightarrow M_{n+1}$ ... (1) through which atoms are bonded to nanoclusters is unlikely to occur and a reaction of $M_n + M_n \rightarrow M_{2n}$ ... (2) is likely to occur. In the above chemical formulae, a subscript indicates the number of constituent atoms. Formula (1) indicates that one atom is bonded to a cluster including n constituent atoms. Formula (2) indicates that a cluster including n constituent atoms and a cluster including n constituent atoms are bonded to form a cluster including 2n constituent atoms.

When the reaction of Formula (1) is dominant, with respect to the particle size distribution immediately after dispersion, a position of the main peak in the particle size distribution after one day is significantly deviated. In this case, although it does not mean association occurs, it does not mean that nanoclusters are uniformly dispersed. Here, "significantly deviated" means that a particle size showing the main peak in the particle size distribution after one day is larger than a particle size showing the main peak in the particle size distribution immediately after dispersion by 20% or more.

Among nanoclusters dispersed in a nanocluster liquid dispersion according to an aspect of the present invention, preferably, 5% or more of the nanoclusters have a predetermined cluster size. That is, a proportion of nanoclusters with a predetermined number of atoms with respect to all nanoclusters is preferably 5% or more.

Among nanoclusters dispersed in a nanocluster liquid dispersion, a ratio of the predetermined nanoclusters can be calculated through liquid chromatography, thin layer chromatography, high performance liquid chromatography, X-ray small angle scattering, dynamic light scattering, electron microscopy, mass spectrometry or the like.

When a case in which high performance liquid chromatography is performed is exemplified, a proportion of nanoclusters with a cluster size showing a representative peak selected from peaks appearing in the high performance liquid chromatograph (HPLC) of the nanocluster liquid dispersion with respect to all nanoclusters is preferably 5% or more. A higher proportion of nanoclusters with a cluster size showing the representative peak is more preferable. For example, a proportion of nanoclusters with a predetermined number of atoms with respect to all nanoclusters is preferably 10% or more, and more preferably 15% or more.

In the field of nanoclusters, when one atom increases, properties and functions of nanoclusters change. Therefore, control of the nanocluster size using the number of atoms as a unit is extremely important. On the other hand, when nanoclusters are generated, nanoclusters with various cluster sizes are generated in many cases. This is because an energy gain according to the growth of nanoclusters is always positive and, nanoclusters grow. That is, it is extremely difficult to control the cluster size. Here, the growth of nanoclusters means that atoms are bonded to nanoclusters and a reaction of $M_n + M \rightarrow M_{n+1} \ldots (1)$ occurs. A nanocluster liquid dispersion in which a cluster size is controlled with high accuracy has not been available until now.

In addition, the fact that a proportion of nanoclusters with a predetermined cluster size among the all nanoclusters is 5% or more means that the number of nanoclusters with a predetermined cluster size is extremely large in consideration of the number of generated nanoclusters. For example, when there is 100 g of a nanocluster liquid dispersion with a concentration of 1 weight %, a weight of nanoclusters included in the liquid dispersion is 1 g, and 5% (50 mg) of them are nanoclusters with a predetermined cluster size. Since the number of atoms included in 1 mol of a material is $6.02 \times 10^{23}$ (Avogadro's number), the number of nanoclusters with a predetermined cluster size is about $6.0 \times 10^{18}$ to $6.02 \times 10^{19}$. That is, it is possible to obtain quite a large number of nanoclusters with a predetermined size from the nanocluster liquid dispersion according to an aspect of the present invention.

On the other hand, in a nanocluster liquid dispersion of the related art, nanoclusters in which neutral atoms aggregate with each other or atomic ion and neutral atoms aggregate in a liquid dispersion are prepared. The nanocluster liquid dispersion of the related art refers to a liquid dispersion prepared by a method in which neutral atoms or atomic ions generated by a magnetron sputtering method are injected into a liquid phase. In principle, since neutral atoms aggregate to each other or atomic ions and neutral atoms aggregate in a liquid, it is extremely difficult to control in units of one atom. In this method also, it is possible to control a nanocluster size to a certain extent by examining various conditions, but it is not possible to control it to the extent of the nanocluster liquid dispersion according to an aspect of the present invention.

A representative peak of the nanocluster can be measured through thin layer chromatography, high performance liquid chromatography, or the like. A procedure of setting a representative peak will be described below based on the example of high performance liquid chromatography.

First, based on measurement results of HPLC, a peak having the highest intensity is set as a first representative peak. An intensity obtained by multiplying an intensity of the first representative peak by 0.9 is set as a threshold value, and when a peak has an intensity that exceeds the threshold value, the peak is set as a representative peak. That is, there may be a plurality of representative peaks.

As will be described below, when a device for producing a nanocluster liquid dispersion according to an aspect of the present invention is used, it is possible to prepare a nanocluster liquid dispersion whose representative peak is isolated as one and a nanocluster liquid dispersion whose representative peaks are intentionally plural.

Various nanoclusters constituting a nanocluster liquid dispersion according to an aspect of the present invention can be used. For example, nanoclusters such as a metal nanocluster consisting of a single metal element, an alloy nanocluster including a plurality of metal elements as constituent elements, and a semiconductor nanocluster including silicon as a constituent element are exemplified. As an example of the semiconductor nanocluster including silicon as a constituent element, a metal-ion-encapsulating silicon cage cluster represented by M@Si (M is a metal ion) is exemplified.

The constituent unit of the nanocluster is preferably a transition metal element or a main group element whose ionization tendency is higher than Ag, or a complex thereof. Examples of the transition metal element whose ionization tendency is higher than Ag include Cr, Fe, Cu, and Ti, examples of the main group element include B, Al, and Si, and examples of the complex thereof include TaSi, TiSi, RuSi, and AlB.

In the method in which neutral atoms or atomic ions generated by a magnetron sputtering method of the related art are injected into a liquid phase, neutral atoms or atomic ions are assumed to aggregate in the liquid phase. However, transition metal elements or main group elements whose ionization tendency is higher than Ag, or complexes thereof are unlikely to aggregate in the liquid phase. Thus, a nanocluster liquid dispersion in which the constituent unit of the nanocluster is a transition metal element or a main group element whose ionization tendency is higher than Ag or a complex thereof cannot be obtained in the method of the related art.

The dispersion medium constituting the nanocluster liquid dispersion may be a solvent having low volatility or a volatile solvent. The solvent having low volatility refers to a solvent with a boiling point of 160° C. or more and a vapor pressure of 100 Pa or less at room temperature. On the other hand, the volatile solvent refers to a solvent whose boiling point is lower than the solvent having low volatility. A liquid dispersion in which nanoclusters are uniformly dispersed in a solvent having low volatility can be particularly appropriately used for applications for which volatilization of a solvent causes a problem such as a radiator. In addition, in consideration of a production process to be described below, the solvent having tow volatility is preferable. On the other hand, the volatile solvent can be particularly appropriately used for applications in which a solvent is removed and a nanocluster film or the like is formed.

The hardly volatile dispersion medium constituting the nanocluster liquid dispersion preferably has an ether bond or a siloxane bond. It is experimentally confirmed that nanoclusters do not easily aggregate in a solvent having oxygen atoms in molecules. It is thought that unshared electron pairs (also referred to as a lone pair of electrons) of oxygen in a molecular chain are coordinately bonded with nanoclusters, and are attached to the surface of nanoclusters, and aggregation between nanoclusters is inhibited. In the case of nanoclusters polarized in a liquid, for example TaSi, TiSi, RuSi or the like, an effect thereof is significant.

More preferably, ends of the ether bond and the siloxane bond have an inert substituent terminal. Termination of the end with an inert substituent refers to termination with an alkyl group, for example, a methyl group. When the ends of the ether bond and the siloxane bond have an inert substituent terminal, it is possible to prevent molecular species used in the dispersion medium from reacting with the nanocluster. That is, it is possible to further suppress denaturation and aggregation of nanoclusters.

On the other hand, in consideration of the use mode, a volatile dispersion medium with a lower boiling point is preferably used. If the volatile solvent is used, it is possible to avoid the residual solvent when a nanocluster film is produced.

As the volatile dispersion medium with a low boiling point constituting the nanocluster liquid dispersion, anyone selected from the group consisting of acyclic ethers, cyclic ethers, acyclic siloxanes, cyclic siloxanes, nitrites, haloalkanes, alcohols, amides, sulfoxides and benzene derivatives is preferable. It has been experimentally confirmed that, in such dispersion mediums, even if a liquid dispersion after nanoclusters are dispersed is left for a long time, the nanoclusters do not aggregate again. That is, it is possible to stably retain the form of a nanocluster liquid dispersion.

As specific examples of the dispersion medium, examples of the acyclic ether include polyethylene glycol, polypropylene glycol, methoxy polyethylene glycol, examples of the acyclic siloxane include polydimethylsiloxane and polymethylphenylsiloxane, examples of the cyclic siloxane include hexamethylcyclotrisiloxane, and decamethylcyclohexasiloxane, examples of the cyclic ether include tetrahydrofuran, and crown ether, examples of the nitriles include acetonitrile and benzonitrile, examples of the haloalkanes include chloroform and dichloromethane, examples of the alcohols include methanol and ethanol, and examples of the benzene derivative include toluene, and dichlorobenzene.

In the nanocluster liquid dispersion according to an aspect of the present invention, it is possible to easily transport nanoclusters with a predetermined cluster size without aggregating, and it is easy to handle when used. In addition, when the cluster size is controlled, a nanocluster film or the like prepared using a nanocluster liquid dispersion can have uniform performance.

In the nanocluster liquid dispersion according to an aspect of the present invention, it is possible to separate nanocluster with a predetermined cluster size with a high yield using high performance liquid chromatography, a recrystallization method, or the like. In addition, since nanoclusters are dispersed in a liquid phase, it is possible to produce a nanocluster film including nanoclusters by a method of coating and the like more easily. That is, it is possible to increase applicability of nanoclusters for various applications such as catalysts, electronic devices, magnetic devices, biosensors, probes, and diagnostic agents (indicators).

Nanocluster Solid Dispersion

Figure 13:
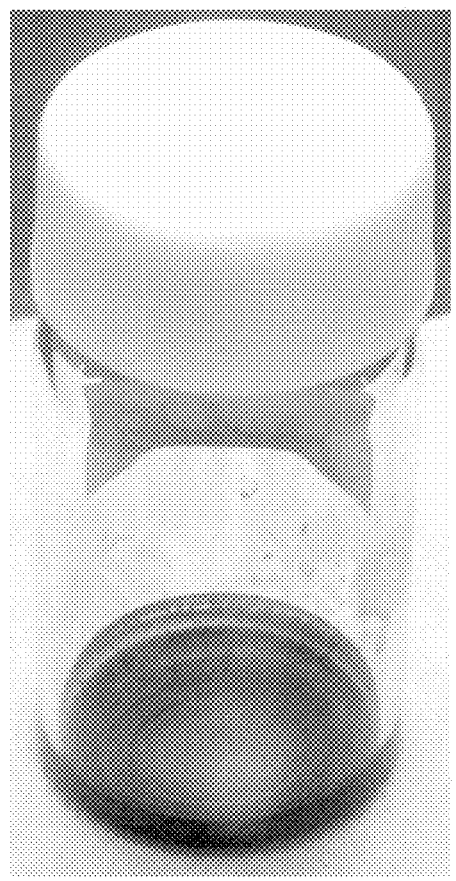
FIG. 13 is a picture of a nanocluster solid dispersion obtained when a dispersion medium of a nanocluster liquid dispersion is removed.

A nanocluster solid dispersion according to an aspect of the present invention mainly includes nanoclusters with a predetermined number of atoms (nanocluster size). The nanocluster solid dispersion is obtained by drying the above nanocluster liquid dispersion. In addition, the dispersion medium may be removed from the liquid dispersion using column chromatography, a recrystallization method, or the like. FIG. 13 is a picture of the nanocluster solid dispersion obtained by drying the nanocluster liquid dispersion. FIG. 13 is a picture of the nanocluster solid dispersion represented by $TaSi_{16}$ as an example.

Here, a proportion of the nanoclusters with a predetermined number of atoms with respect to all nanoclusters included in the nanocluster solid dispersion is preferably 5% or more, more preferably 10% or more, and most preferably 15% or more.

The nanocluster solid dispersion is put into the dispersion medium to prepare a nanocluster liquid dispersion. That is, nanoclusters constituting the nanocluster solid dispersion do not aggregate with each other.

The surface of nanoclusters constituting the nanocluster solid dispersion is covered with an organic substance. The organic substance may be a molecule constituting the dispersion medium or a protective agent that is intentionally added in a process of producing a liquid dispersion. When the surface of nanoclusters is covered with the organic substance, it is possible to prevent nanoclusters from aggregating with each other in a dried state.

Nanocluster Dispersion Film

Figure 14:
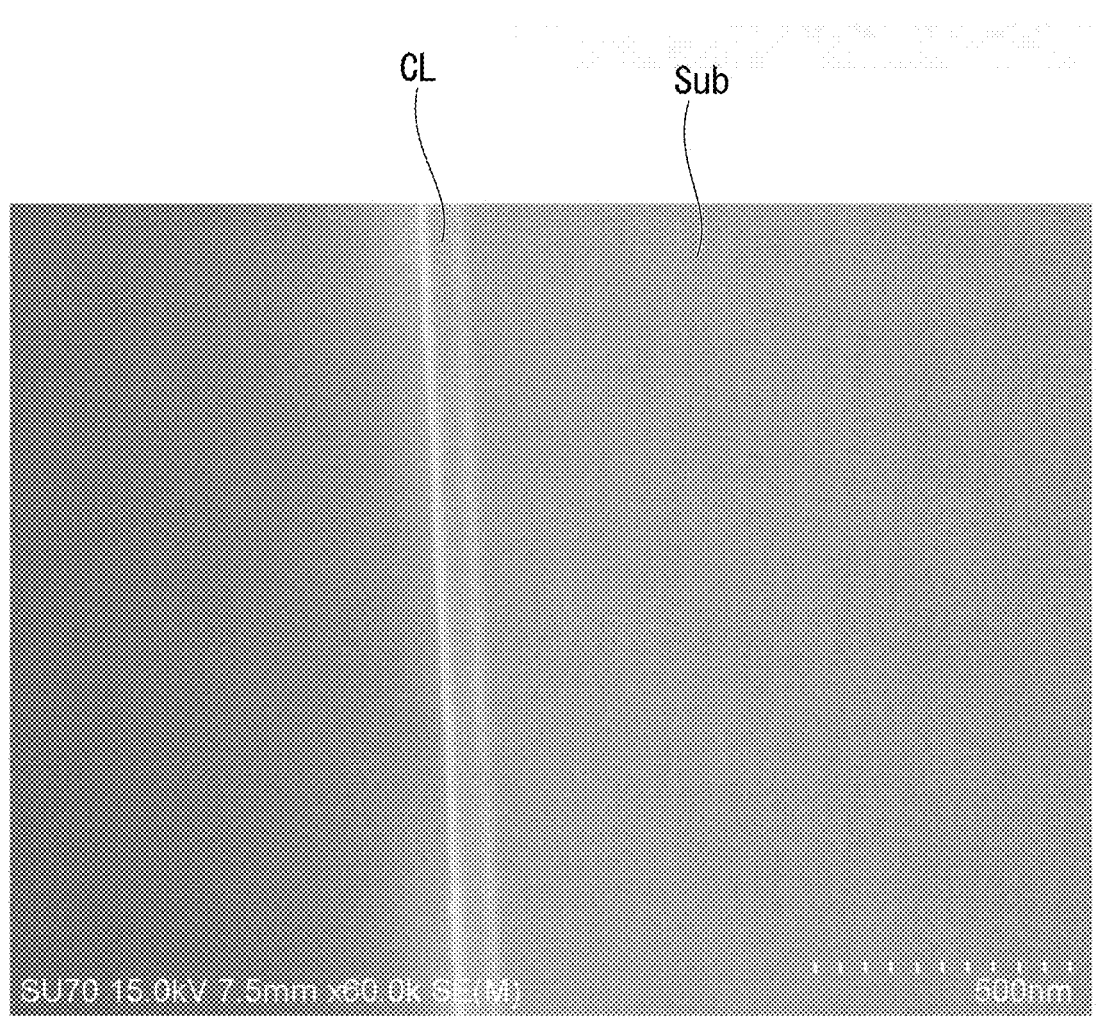
FIG. 14 is a picture of a nanocluster dispersion film obtained when a dispersion medium of a nanocluster liquid dispersion is removed.

A nanocluster dispersion film according to an aspect of the present invention is formed by applying a nanocluster liquid dispersion on a substrate. The nanocluster dispersion film mainly includes nanoclusters with a predetermined number of atoms (nanocluster size). According to applications, the dispersion medium in the liquid dispersion may be removed. FIG. 14 is a picture of a nanocluster dispersion film obtained by spin coating a nanocluster liquid dispersion. In the nanocluster dispersion film shown in FIG. 14, a nanocluster dispersion film CL with a thickness of 60 nm is formed on a Si substrate Sub.

As described above, 5% or more of nanoclusters dispersed in the nanocluster liquid dispersion with respect to all generated nanoclusters have a predetermined nanocluster size. Therefore, a proportion of nanoclusters with a predetermined nanocluster size constituting the nanocluster dispersion film with respect to all nanoclusters is 5% or more. In addition, according to high performance liquid chromatography or a recrystallization method, a liquid dispersion in which a content of nanoclusters with a predetermined cluster size increases is used, and thus it is possible to increase a proportion of nanoclusters with a predetermined nanocluster size constituting the dispersion film. A proportion of nanoclusters with a predetermined nanocluster size constituting the nanocluster dispersion film with respect to all nanoclusters is preferably 10% or more and more preferably 15% or more.

Device for Producing a Nanocluster Liquid Dispersion

A device for producing a nanocluster liquid dispersion includes a nanocluster generation unit and a nanocluster collection unit that is arranged in a direction in which nanoclusters generated in the nanocluster generation unit travel.

The nanocluster generation unit generates nanoclusters in a gas phase. A generation method is not particularly limited and various methods can be used. For example, a DC discharging method, a laser evaporation method, an ion sputtering method, or a vacuum evaporation method using a Knudsen cell or the like can be used.

As the nanocluster generation unit, a nanocluster generation device described in Patent Document 3 is preferably used. Specifically, the nanocluster generation unit preferably includes a vacuum chamber, a sputtering source, a power supply, a first inert gas supply unit, and a nanocluster growth cell. The sputtering source performs magnetron sputtering and generates a plasma. A target is provided on a cathode of the sputtering source. The power supply supplies power to the sputtering source. The first inert gas supply unit supplies a first inert gas to the sputtering source. The nanocluster growth cell is housed in the vacuum chamber. In addition, as necessary, a second inert gas introduction unit configured to introduce a second inert gas in the nanocluster growth cell may be included. In magnetron sputtering, in order to increase uniformity of generated nanoclusters, pulse discharging is preferably performed.

In a device for producing nanocluster liquid dispersion, the nanoclusters generated in the nanocluster generation unit are collected in the nanocluster collection unit without change. When a cluster size of the nanoclusters generated in the nanocluster generation unit is uniform, the cluster size in the obtained nanocluster liquid dispersion is controlled.

A case in which the nanocluster generation device described in Patent Document 3 which is an aspect of the nanocluster generation unit is used will be described below in detail with reference to the drawings.

First Embodiment

FIG. 1 is a schematic cross-sectional view of a device for producing a nanocluster liquid dispersion according to a first embodiment. A device for producing a nanocluster liquid dispersion 100 according to the first embodiment includes a nanocluster generation unit 10 and a nanocluster collection unit 20.

The nanocluster generation unit 10 includes a vacuum chamber 11, a nanocluster growth cell 12, a sputtering source 13, a liquid nitrogen jacket 14, a control device 15, a pulse power supply 16, a first inert gas introduction unit 17, and a second inert gas introduction unit 18.

As the vacuum chamber 11, a known vacuum chamber can be used. An exhaust unit 19 is connected to the vacuum chamber 11. The exhaust unit 19 increases a degree of vacuum in the vacuum chamber 11. As the exhaust unit 19, a turbo molecular pump or the like can be used. The exhaust unit 19 can increase a degree of vacuum in the vacuum chamber 11 to, for example, a $10^{-1}$ to $10^{-4}$ Pa.

The nanocluster growth cell 12 is installed in the vacuum chamber 11. The outer circumference of the nanocluster growth cell 12 is surrounded by the liquid nitrogen jacket 14. Liquid nitrogen ($N_2$) flows in a region surrounded by the outer circumference of the nanocluster growth cell 12 and the inner circumference of the liquid nitrogen jacket 14. When liquid nitrogen flows in the region, it is possible to prevent a temperature in the nanocluster growth cell 12 from increasing and it is possible to cool helium supplied from the second inert gas introduction unit 18 to be described below.

The sputtering source 13 includes a target 131, an anode 132, and a magnet unit 133. The sputtering source 13 is arranged inside the nanocluster growth cell 12 that is arranged in the vacuum chamber 11. The sputtering source 13 is freely movable in a tube axis direction in the nanocluster growth cell 12. Thus, it is possible to freely set a stretching distance of a region in which nanoclusters grow in the tube axis direction. In other words, it is possible to freely set a length of a growth region that is a distance from the surface of the target 131 to a nanocluster outlet 121 of the nanocluster growth cell 12.

The target 131 functions as a cathode and is connected to the pulse power supply 16. The pulse power supply 16 is controlled by the control device 15. When power with a pulse is supplied from the pulse power supply 16 to the sputtering source 13, a voltage is applied between the target 131 and the anode 132. The magnet unit 133 applies a magnetic field to the vicinity of the surface of the target 131.

A material used for the target 131 can be variously changed according to nanoclusters to be prepared. For example, in order to prepare platinum nanoclusters, platinum is used for the target 131, and in order to prepare TaSi nanoclusters, TaSi is used for the target 131.

The control device 15 controls the pulse power supply 16. The pulse power supply 16 applies a voltage at an on time $t_{on}$ and stops voltage application at an off time $t_{off}$ according to an on signal and an off signal from the control device 15, and applies a voltage with a pulse to the sputtering source 13. For example, as the pulse power supply 16, a modulated pulse power supply that can control power according to a duty ratio ($t_{on}/t_{on}+t_{off}$) and a DC voltage DCV can be used.

When a duty ratio ($t_{on}/t_{on}+t_{off}$) of the pulse signal of the pulse power supply 16 and the like are changed, it is possible to separately form a nanocluster liquid dispersion having one representative peak and a nanocluster liquid dispersion having two or more representative peaks.

The first inert gas introduction unit 17 is a gas flow path of which an end is arranged between the target 131 and the anode 132. The gas flow path can be constituted by a known pipe or the like. In FIG. 1, an inlet of the first inert gas introduction unit 17 is provided at only one place between the target 131 and the anode 132. The first inert gas introduction unit 17 is not limited to this configuration, and the first inert gas introduction unit 17 may be branched along the way with inlets provided at a plurality of places. A configuration in which a first inert gas can be introduced to the surface of the target 131 may be used.

The first inert gas may be any gas that can be used for general sputtering, and argon gas can be generally used.

When a first inert gas is supplied from the first inert gas introduction unit 17 to the surface of the target 131, strong glow discharging is generated in the vicinity of the surface of the target 131. When the first inert gas is ionized due to the glow discharging and collides with the target 131, sputtered particles are released from the target. The sputtered particles are made of neutral atoms, ions and the like derived from the target 131.

The second inert gas introduction unit is a gas flow path which spirally circulates inside the liquid nitrogen jacket 14 and whose end protrudes into the nanocluster growth cell 12. The gas flow path can be constituted by a known pipe or the like. The second inert gas is not particularly limited as long as it is a gas species that does not react with the generated sputtered particles. For example, helium gas or the like can be appropriately used.

The second inert gas introduction unit 18 supplies a second inert gas that is cooled by liquid nitrogen into the nanocluster growth cell 12. The second inert gas introduction unit 18 is preferably controlled by a pressure gauge, a mass flow controller, or the like. A pressure in the nanocluster growth cell 12 can be maintained at about 10 to 40 Pa by the pressure gauge or the like.

The second inert gas introduced from the second inert gas introduction unit 18 has a certain flow direction and the sputtered particles generated in the target 131 move in the flow direction. In this case, in a second inert gas atmosphere, the sputtered particles are bonded to each other and various nanoclusters are generated.

As described in Patent Document 3, the nanocluster size can be freely selected by controlling discharging power in the sputtering source 13, a duty ratio in the pulse power supply 16, a length of a growth region in the nanocluster growth cell 12, a flow rate of the first inert gas supplied from the first inert gas introduction unit 17, a flow rate of the second inert gas supplied from the second inert gas introduction unit 18, and the like.

The nanocluster collection unit 20 shown in FIG. 1 includes a storage chamber 21 in which a dispersion medium 23 can be stored, and a stirring bar 22 for flowing the dispersion medium 23 of nanoclusters. The stirring bar 22 is an aspect of a flowing unit in the scope of the claims.

The nanocluster collection unit 20 is arranged in direction in which nanocluster generated in the nanocluster generation unit 10 travel. While the nanocluster collection unit 20 is arranged in the vacuum chamber 11 constituting the nanocluster generation unit 10 in FIG. 1, it may be arranged in another chamber connected to the side of the vacuum chamber 11 in the direction in which nanoclusters travel.

The nanocluster collection unit 20 collects nanoclusters in the dispersion medium 23 without aggregating. Thus, when the nanocluster size is controlled in the nanocluster generation unit 10, it is possible to isolate desired nanoclusters.

The storage chamber 21 is a container in which the dispersion medium 23 is stored. The storage chamber 21 is preferably made of a material that does not serve as a gas generation source in the vacuum chamber. For example, a material such as stainless steel, glass, or the like can be used for the storage chamber 21.

It is possible to appropriately set a capacity at which the dispersion medium 23 of the storage chamber 21 can be stored. When the capacity is too small, there is an increased risk of nanoclusters aggregating in the dispersion medium 23. That is, a yield of nanoclusters with a desired nanocluster size decreases. On the other hand, when the capacity is too large, it is necessary to continue sputtering for about several days to several weeks in order to obtain a liquid dispersion in which nanoclusters are dispersed at a high concentration. For example, when a time average discharging power of the pulse power supply 16 is 300 W, a flow rate of the first inert gas is 70 sccm, and a flow rate of the second inert gas is 0 sccm, an amount of the dispersion medium 23 is preferably 40 ml or more.

Figure 2:
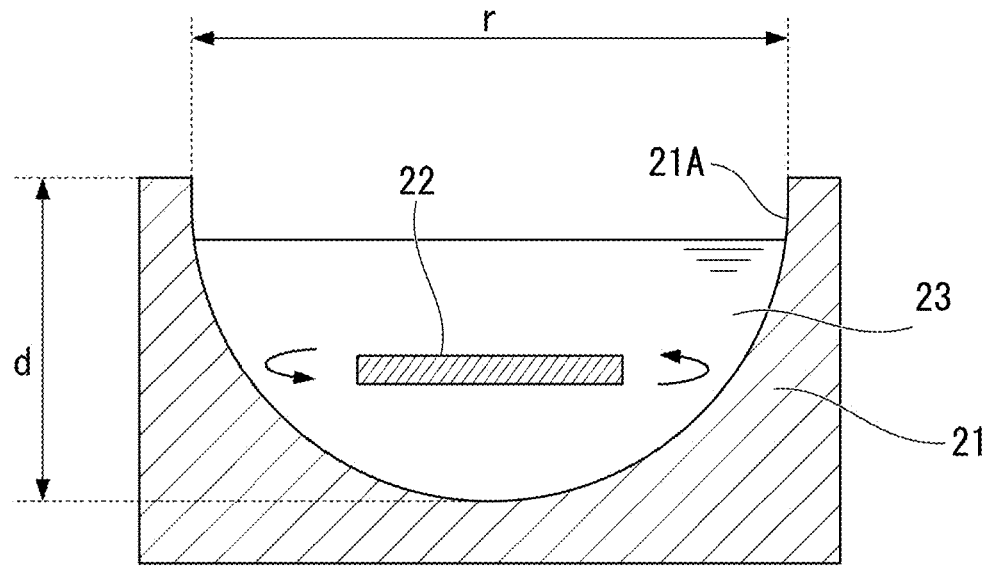
FIG. 2 is a schematic cross-sectional view of a storage chamber in the device for producing a nanocluster liquid dispersion according to the first embodiment.

FIG. 2 is a schematic cross-sectional view of a storage chamber of the device for producing a nanocluster liquid dispersion according to the first embodiment of the present invention.

The shape of the storage chamber 21 in a plan view in the direction in which nanoclusters travel may be a circular shape or a rectangular shape. When the storage chamber 21 is viewed in a plan view in the direction in which nanoclusters travel, a diameter r of a circle inscribed in the storage chamber 21 is preferably 60 mm or more. The sputtered particles generated in the target 131 generate nanoclusters in the nanocluster growth cell 12. The generated nanoclusters are released from the nanocluster outlet 121 to the vacuum chamber 11 with a high degree of vacuum and move toward the storage chamber 21. When the diameter of the nanocluster outlet 121 is 12 mm, and the distance between the nanocluster outlet 121 and the storage chamber 21 is 90 mm, a spatial extent of nanoclusters on the surface of the dispersion medium 23 falls within a range of a circle with a diameter of 40 mm around a center axis of the cluster growth cell 12. Thus, when the diameter r of the circle inscribed in the storage chamber 21 is 60 mm or more, it is possible to collect the generated nanoclusters without leakage.

When flow rates of the first and second inert gases are high, or when the length of the growth region in the nanocluster growth cell 12 is long, a case in which a position at which nanoclusters are incident is not fallen within a range of a circle with a diameter of 40 mm can be conceivable. In this case, preferably, a position of the storage chamber 21 in the tube axis direction is set close to the nanocluster outlet 121 so that nanoclusters can be collected without leakage, or the diameter of the circle inscribed in the storage chamber 21 is set to be larger.

A depth d of the storage chamber 21 is preferably 2 cm or more. The generated nanoclusters are collected in the dispersion medium 23 stored in the storage chamber 21. A depth from a liquid surface of the dispersion medium 23 to the bottom of the storage chamber 21 is preferably 2 cm or more although it depends on a generation rate of the nanoclusters that are incident on the dispersion medium 23 and a rotational speed of the stirring bar 22. This is because the incident nanoclusters do not reach the bottom of the storage chamber 21 and the nanoclusters are appropriately dispersed in the dispersion medium 23. While it is possible to lower a generation rate of nanoclusters that are incident on the dispersion medium 23, a yield per unit time of nanoclusters decreases.

An inner wall 21A in which the dispersion medium 23 of the storage chamber 21 is stored is preferably formed of a curved surface as shown in FIG. 2. When the shape of the inner wall 21A is formed in a curved surface, it is possible to secure an area in a plan view when viewed the direction in which nanoclusters travel and prevent the capacity of the dispersion medium 23 from increasing too much.

The storage chamber 21 preferably includes a liquid spill prevention structure that prevents the dispersion medium 23 from spilling out of the storage chamber 21. This is because, when the dispersion medium 23 spills out of the storage chamber 21, an amount of the dispersion medium 23 in the storage chamber 21 decreases and there is an increased risk of aggregation.

Figure 3:
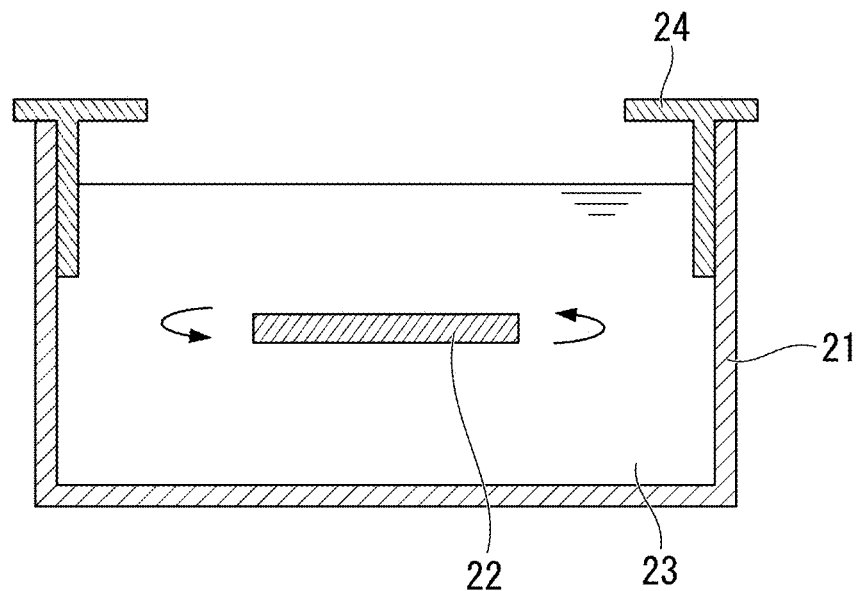
FIG. 3 is a schematic cross-sectional view of another form of the storage chamber in the device for producing a nanocluster liquid dispersion according to the first embodiment.

As the liquid spill prevention structure, for example, as shown in FIG. 3, a lid 24 having an opening may be provided in the storage chamber 21. In order to return the dispersion medium adhered to the inner wall of the lid 24 into the storage chamber 21, the inner wall of the lid 24 is preferably arranged inside the inner wall of the storage chamber 21.

Since nanoclusters are incident on the dispersion medium 23 through the opening, the diameter of the opening is preferably 40 mm or more.

The liquid spill prevention structure is not limited to this form, and, for example, an inclined surface that increases in diameter from the uppermost part of the storage chamber 21 may be provided. In this structure, the dispersion medium 23 overflowing from the storage chamber 21 is supplied again into the storage chamber 21 along the inclined surface.

The storage chamber 21 is preferably arranged so that a center position on the storage chamber 21 and the nanocluster outlet 121 do no overlap in a plan view, and the center position of the storage chamber 21 and the nanocluster outlet 121 are preferably separated by 20 mm or more in a plan view.

Nanoclusters generated in a nanocluster generation device 10 are emitted in the form of a beam from the nanocluster outlet 121. On the other hand, the dispersion medium 23 stored in the storage chamber 21 is rotated by the stirring bar 22. According to rotation by the stirring bar 22, a liquid amount of the dispersion medium 23 decreases at the central part and increases at the peripheral part of the storage chamber 21. In addition, a flow rate of the dispersion medium 23 is higher at the peripheral part than at the center. When the storage chamber 21 is arranged so that the center position of the storage chamber 21 and the nanocluster outlet 121 do not overlap in a plan view, it is possible to ensure a sufficient liquid amount of apart on which nanoclusters are incident. In addition, since a flow rate of the part (peripheral part) is high, dispersibility of nanoclusters in the dispersion medium 23 is further improved.

The stirring bar 22 rotates the dispersion medium 23 stored in the storage chamber 21. A direction in which the stirring bar 22 rotates the dispersion medium 23 is an in-plane direction perpendicular to the direction in which nanoclusters travel. That is, the dispersion medium 23 of nanoclusters always flows in the direction in which nanoclusters travel. When the dispersion medium 23 flows, a concentration of nanoclusters on the surface on which nanoclusters are incident is prevented from being extremely higher. As a result, aggregation of nanoclusters on the incidence surface of the dispersion medium 23 and inside the dispersion medium 23 is avoided.

The rotational speed of the stirring bar 22 is set as a rotational speed at which nanoclusters do not aggregate in the dispersion medium 23. The rotational speed at which nanoclusters do not aggregate differs according to a volume of the storage chamber 21, a type of a solution of the dispersion medium 23, a generation rate of nanoclusters that are incident, and the like, and an appropriate rotational speed can be confirmed by a prior examination. When it is described that nanoclusters do not aggregate, this means that a cluster size of a representative peak of nanoclusters collected in the dispersion medium 23 is not larger than a cluster size of a representative peak of nanoclusters in a gas phase state prepared in the nanocluster generation unit 10 by 10% or more. Determination of whether nanoclusters have aggregated with each other can be confirmed according to whether precipitation has occurred in the dispersion medium 23.

For example, when the storage chamber 21 has a cylindrical shape with a diameter of 90 mm, the stirring bar 22 has a size of 8 mm in diameter and 40 mm in length, and the dispersion medium 23 is polyethylene glycol, the rotational speed of the stirring bar 22 is preferably 400 rpm or more and 1000 rpm or less. In this case, when the rotational speed of the stirring bar 22 is less than 400 rpm, aggregation of nanoclusters proceeds and precipitation in the dispersion medium 23 is confirmed. On the other hand, when the rotational speed exceeds 1000 rpm, rotation becomes faster and there is an increased risk of a liquid spilling out.

As the dispersion medium 23 stored in the storage chamber 21, dispersion mediums constituting the above nanocluster liquid dispersion can be used. Among them, a dispersion medium is preferably a solvent having low volatility with a boiling point of 160° C. or more and a vapor pressure of 100 Pa or less at room temperature. The dispersion medium 23 is stored in the storage chamber 21 provided in the vacuum chamber 11. When a boiling point of the dispersion medium 23 is low, an amount of the dispersion medium 23 decreases with the passages of time, and there is an increased risk of nanoclusters aggregating the dispersion medium 23.

A detection unit 30 configured to detect nanoclusters may be provided between the nanocluster generation unit 10 and the nanocluster collection unit 20. The detection unit 30 is a probe plate that is retractable in the vertical direction with respect to the direction in which nanoclusters travel.

When the detection unit 30 as a probe plate is inserted between the nanocluster outlet 121 of the nanocluster generation unit 10 and the storage chamber 21 of the nanocluster collection unit 20, nanoclusters emitted from the nanocluster outlet 121 collide on the probe plate. For example, when Ta and Si are used as elements constituting nanoclusters, if nanoclusters are appropriately generated, the probe plate is colored. On the other hand, if nanoclusters are not appropriately generated, a transparent film is formed on the surface of the probe plate.

The detection unit 30 confirms whether desired nanoclusters have been generated. When it is confirmed using the detection unit 30 that desired nanoclusters are generated in the nanocluster generation unit 10, it is possible to increase a concentration of nanoclusters with a desired cluster size in the obtained nanocluster liquid dispersion.

In the device for producing a nanocluster liquid dispersion 100 according to the first embodiment, the nanocluster size can be controlled by the nanocluster generation unit 10 and the nanoclusters can be dispersed without aggregating by the nanocluster collection unit 20. That is, it is possible to isolate nanoclusters with a desired cluster size.

Second Embodiment

Figure 4:
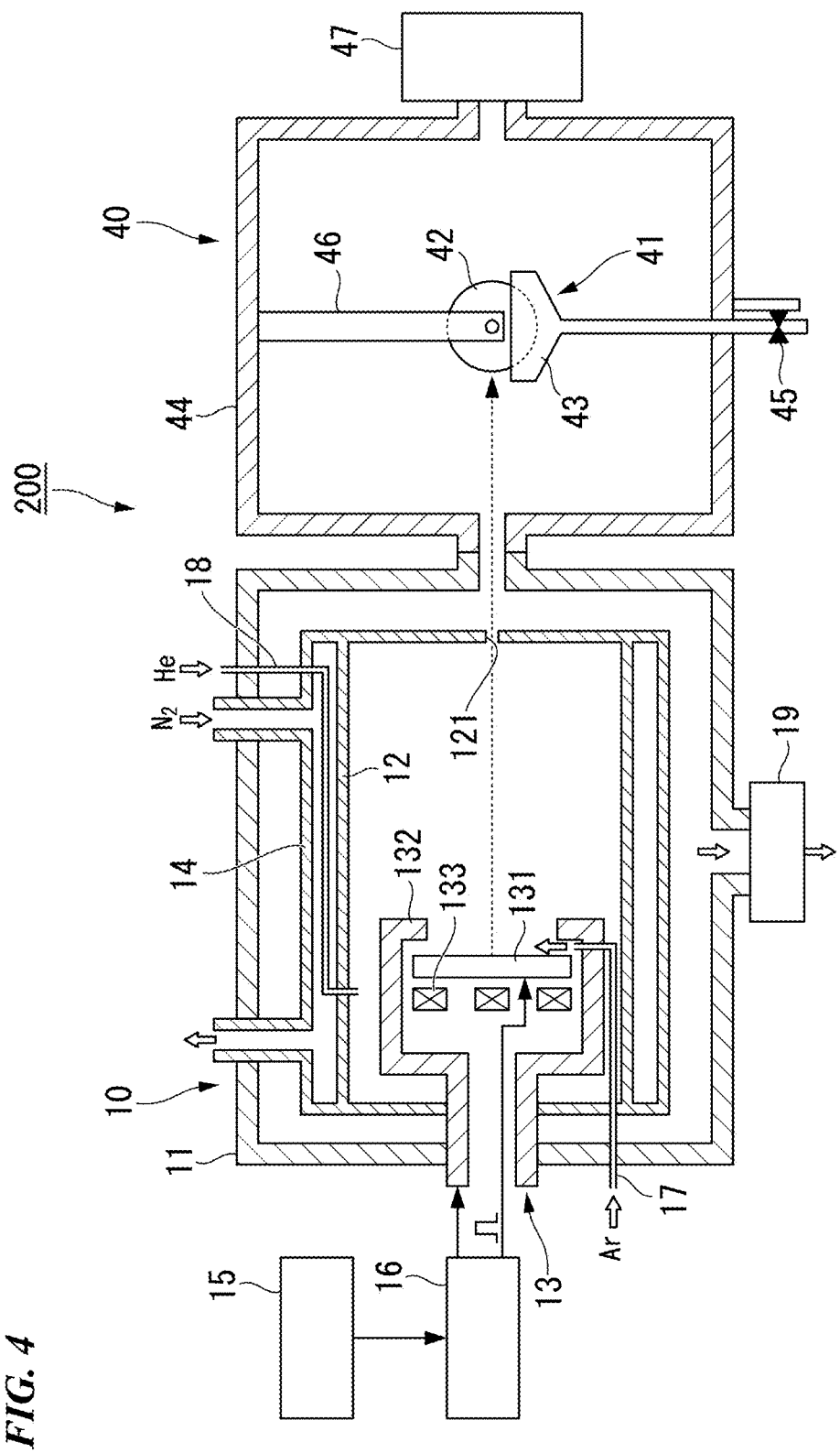
FIG. 4 is a schematic cross-sectional view of a device for producing a nanocluster liquid dispersion according to a second embodiment.

FIG. 4 is a schematic cross-sectional view of a device for producing a nanocluster liquid dispersion according to a second embodiment. A difference between a device for producing a nanocluster liquid dispersion 200 according to the second embodiment and the device for producing a nanocluster liquid dispersion 100 according to the first embodiment is a nanocluster collection unit 40. Description of the same parts as in the first embodiment will be omitted below.

The configuration of the nanocluster generation unit 10 is the same as that in the first embodiment. The only difference is that the nanocluster generation unit 10 is of a vertical type in the first embodiment and is of a horizontal type in the second embodiment. The nanocluster generation unit 10 may also be of a vertical type in the second embodiment.

The nanocluster collection unit 40 in the device for producing a nanocluster liquid dispersion 200 according to the second embodiment includes a storage chamber 41 and a rotating body 42. In FIG. 4, a dispersion medium 43 is stored in the storage chamber 41. The vacuum chamber 11 constituting the nanocluster generation unit 10 and a vacuum chamber 44 constituting the nanocluster collection unit 40 are shown as separate members in FIG. 4, but they may be one large chamber. An exhaust device 47 for increasing a degree of vacuum of the inside is connected to the vacuum chamber 44. As the exhaust device 47, a turbo molecular pump or the like can be used. The exhaust device 47 can increase a degree of vacuum in the vacuum chamber 44 to, for example, $10^{-2}$ to $10^{-6}$ Pa.

The size, shape, and the like of the storage chamber 41 can be the same as those in the storage chamber 21 of the first embodiment. As shown in FIG. 4, a configuration in which a flow path is provided below the storage chamber 41, and the dispersion medium 43 stored in the storage chamber 41 can be easily discharged by opening a petcock 45 may be used. The same dispersion medium as in the first embodiment can be used as a dispersion medium stored.

The rotating body 42 is a rotating body having an axis of rotation in a direction perpendicular to the direction in which nanoclusters travel. The rotating body 42 is an aspect of a flowing unit in the scope of the claims. The rotating body 42 is supported by a support 46 and is disposed so that a part thereof is immersed in the dispersion medium stored in the storage chamber 41. In FIG. 4, the support 46 supports the rotating body from above, but it is not limited to this form. The support 46 may support the rotating body 42 from below or side. In consideration of maintenance, the support 46 preferably supports the rotating body 42 from below. Preferably, the rotating body 42 and the support 46 are freely attachable. This is because it is preferable to replace the rotating body 42 for each type of the dispersion medium used and for each type of the nanocluster.

Figure 5:
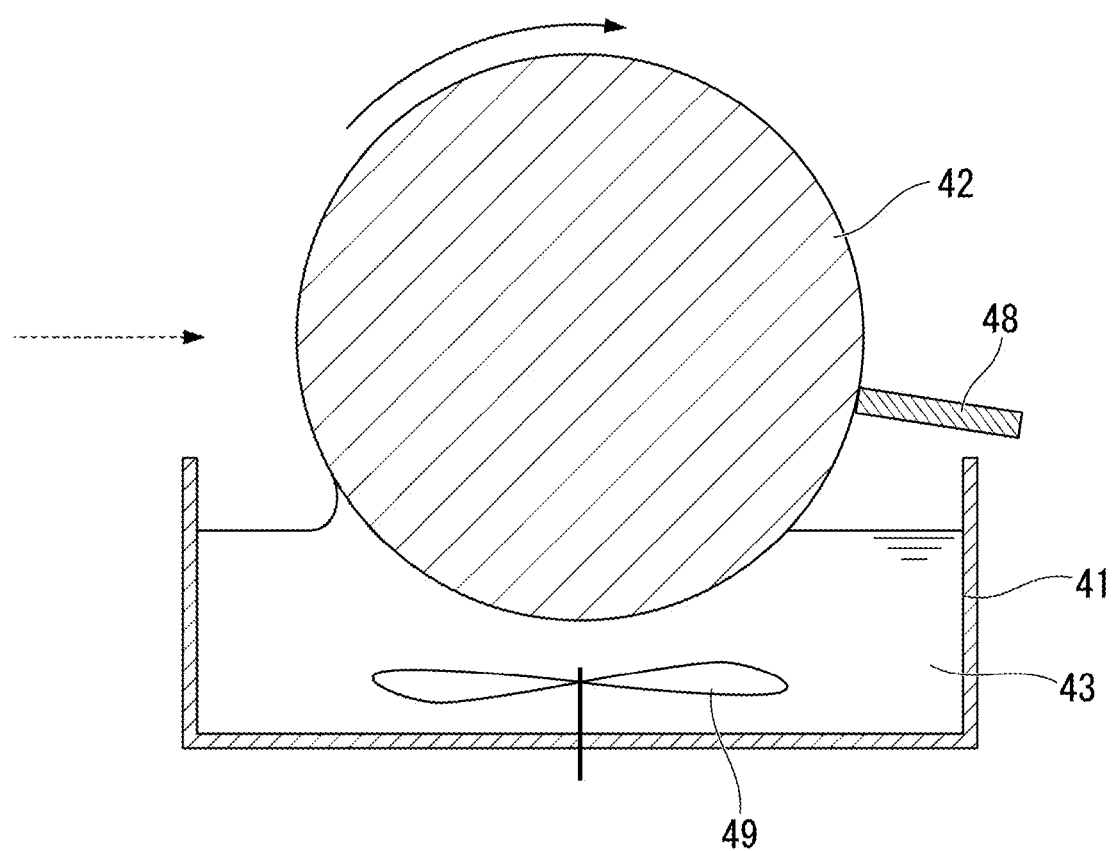
FIG. 5 is a schematic cross-sectional view of an enlarged nanocluster collection unit according to the second embodiment.

FIG. 5 is a schematic cross-sectional view in which a part of the nanocluster collection unit 40 according to the second embodiment is enlarged. As shown in FIG. 5, when the rotating body 42 rotates, the dispersion medium 43 stored in the storage chamber 41 is pulled up. The pulled-up dispersion medium 43 follows the surface of the rotating body 42 according to the rotation of the rotating body 42.

Nanoclusters emitted from the nanocluster outlet 121 of the nanocluster generation unit 10 are incident on a side surface of the rotating body 42. A liquid dispersion with a high nanocluster concentration on the surface on which one nanocluster is incident the rotating body 42 is transported in the rotation direction. Thus, when the next nanocluster is incident, it is possible to lower a nanocluster concentration on the incidence surface. That is, a nanocluster concentration on the surface on which nanocluster are incident is prevented from being extremely higher. When a nanocluster concentration is prevented from being extremely higher at a part, aggregation of nanoclusters on the incidence surface of the dispersion medium 43 and inside the dispersion medium 43 is avoided.

The rotational speed of the rotating body 42 is set as a rotational speed at which nanoclusters do not aggregate in the dispersion medium 43. A higher rotational speed of the rotating body 42 is preferable.

The rotational speed at which nanoclusters do not aggregate differs according to a volume of the storage chamber 41, an amount of the dispersion medium 43 pulled-up on the surface of the rotating body 42, a type of a solution of the dispersion medium 43, a speed of nanoclusters that are incident, and the like. An appropriate level of the rotational speed can be confirmed by a prior examination. When the rotational speed is higher, it is possible to increase an amount of the dispersion medium 43 pulled-up on the surface of the rotating body 42. When the liquid dispersion is efficiently transported in the rotation direction, it is possible to prevent the occurrence of a part in which a nanocluster concentration is high locally.

Diamond-like carbon is preferably applied to the surface of the rotating body 42. When diamond-like carbon is applied, it is possible to increase wettability of the dispersion medium 43 and it is possible to increase an amount of the dispersion medium 43 pulled-up on the surface of the rotating body 42.

The interior of the rotating body 42 preferably has a hollow structure. When the interior of the rotating body 42 has a hollow structure, it is possible to reduce a weight of the rotating body 42 and increase a rotational speed.

A position at which the rotating body 42 is disposed is preferably within 350 mm from the nanocluster outlet 121. When the position is too far from the nanocluster outlet 121, nanoclusters diffuse and do not collide on the surface of the rotating body 42 appropriately.

A squeegee 48 is preferably provided behind the rotating body 42 in the rotation direction. The squeegee 48 may be supported by the support 46 or may be connected to another part and supported. The squeegee 48 is substantially in close contact with the rotating body 42 and it is preferable to control a distance lo the rotating body 42 with an accuracy of 0.1 mm or less.

The squeegee 48 removes apart of the dispersion medium 43 applied to the surface of the rotating body 42. The dispersion medium 43 is a liquid dispersion after nanoclusters are dispersed. When the squeegee 48 is provided, it is possible to separate the dispersion medium 43 pulled-up on the rotating body 42 and the liquid dispersion after nanoclusters are dispersed. A liquid dispersion separated by providing a guide plate or the like may be prevented from being mixed into inside the storage chamber 41.

Preferably, in the storage chamber 41, a stirring unit 49 configured to stir the dispersion medium 43 stored in the storage chamber 41 may be provided. As shown in FIG. 5, the staring unit 49 may be a stirring blade provided below the rotating body 42, a stirring bar, or the like. When the stored dispersion medium 43 is stirred by the stirring unit 49, it is possible to obtain a uniform concentration of nanoclusters dispersed in the dispersion medium 43.

In the device for producing a nanocluster liquid dispersion 200 according to the second embodiment, the detection unit may also be provided.

In the device for producing a nanocluster liquid dispersion 200 according to the second embodiment, the nanocluster size can be controlled by the nanocluster generation unit 10. In addition, according to the rotating body 42 of the nanocluster collection unit 40, the dispersion medium 43 on the surface on which nanoclusters are incident can flow about at a speed at which nanoclusters do not aggregate on the surface of the dispersion medium 43. Accordingly, it is possible to prepare a nanocluster liquid dispersion on which nanoclusters are incident the dispersion medium 43 do not aggregate, but they are uniformly dispersed. That is, it is possible to isolate nanoclusters with a desired cluster size.

Third Embodiment

Figure 6:
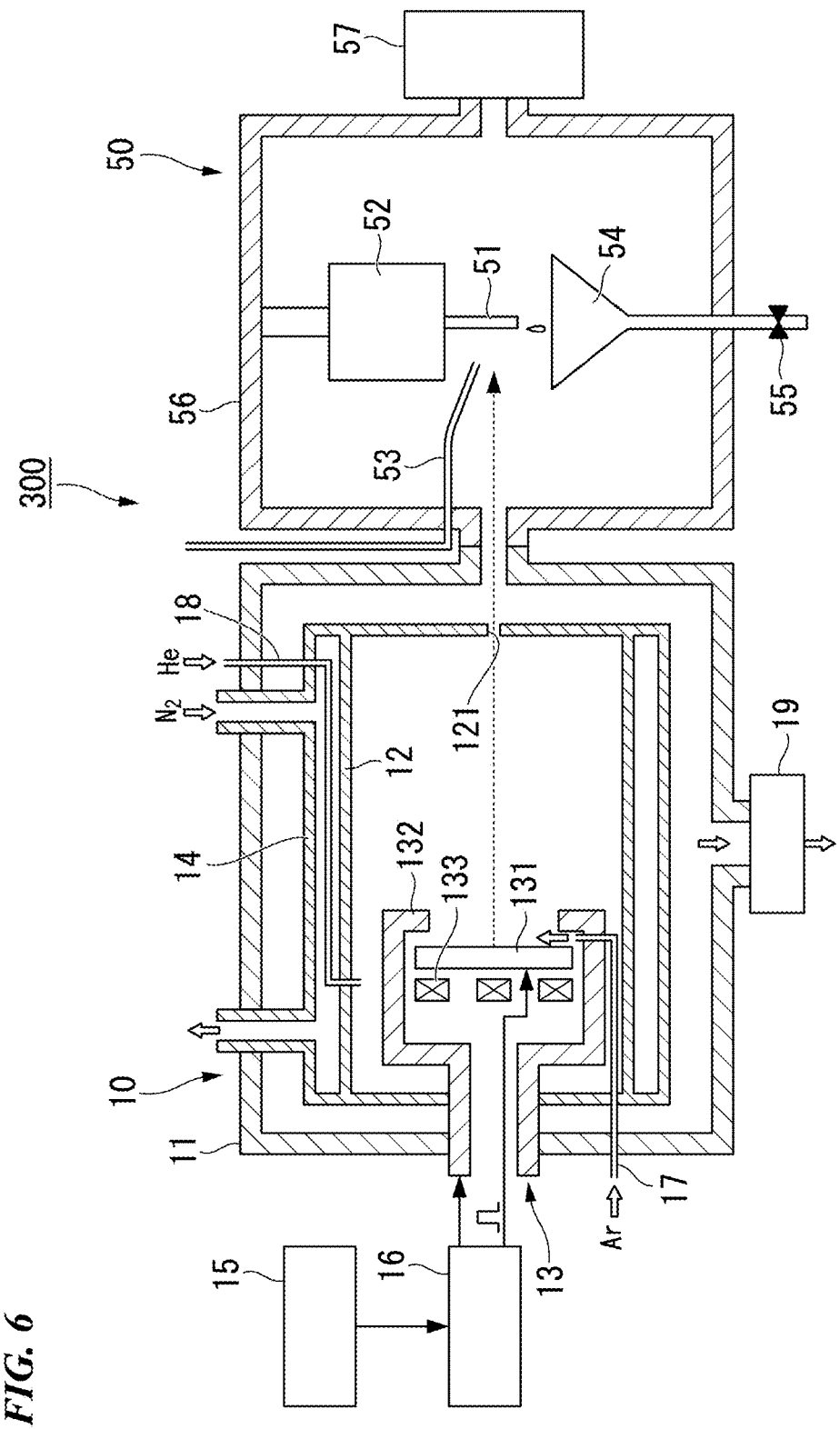
FIG. 6 is a schematic cross-sectional view of a device for producing a nanocluster liquid dispersion according to a third embodiment.

FIG. 6 is a schematic cross-sectional view of a device for producing a nanocluster liquid dispersion according to a third embodiment. A difference between a device for producing a nanocluster liquid dispersion 300 according to the third embodiment and the device for producing a nanocluster liquid dispersion 100 according to the first embodiment is a nanocluster collection unit 50. Description of the same parts as in the first embodiment will be omitted below.

The nanocluster generation unit 10 in the third embodiment is of a horizontal type as in the second embodiment.

The nanocluster collection unit 50 includes a substrate 51, a cooling mechanism 52, a dispersion medium supply unit 53, and a collection container 54. In FIG. 6, the vacuum chamber 11 constituting the nanocluster generation unit 10 and a vacuum chamber 56 constituting the nanocluster collection unit 50 are shown as separate members, but they may be one large chamber. The exhaust device 57 for increasing a degree of vacuum in the inside is connected to the vacuum chamber 56. As the exhaust device 57, a turbo molecular pump or the like can be used. The exhaust device 57 can increase a degree of vacuum in the vacuum chamber 56 to, for example, $10^{-2}$ to $10^{-6}$ Pa.

The substrate 51 is arranged to cross the direction in which nanoclusters travel. The material of the substrate 51 is preferably a material with favorable conductivity, and oxygen-free copper or the like can be used.

A dispersion medium is sprayed onto the substrate 51 from the dispersion medium supply unit 53. As the dispersion medium, a highly volatile solvent can also be used in addition to the same dispersion medium as in the first embodiment. For example, tetrahydrofuran can be used. In the third embodiment, since the dispersion medium is not stored, but it is sprayed, a solvent that is more volatile than the dispersion mediums of the first embodiment and the second embodiment can be used.

One end of the dispersion medium supply unit 53 is connected to an external tank in which a dispersion medium is stored and the other end thereof is provided in the vicinity of the substrate 51. When the dispersion medium supplied from the dispersion medium supply unit 53 is sprayed onto the substrate 51, it is cooled by the cooling mechanism 52 and becomes a solid. At this time, nanoclusters and the dispersion medium are co-deposited, and the nanoclusters are dispersed in a solvent matrix. Then, when the solvent matrix is dissolved, a liquid dispersion is obtained. As the cooling mechanism 52, a known cold trap or the like can be used.

The nanocluster and the dispersion medium that are co-deposited on the surface of the substrate 51 become a nanocluster liquid dispersion when the substrate 51 is heated. The nanocluster liquid dispersion flows on the surface of the substrate 51 and is added dropwise to the collection container 54. A configuration in which a flow path is provided below the collection container 54 and the liquid dispersion collected in the collection container 54 can be easily discharged by opening a petcock 55 may be used.

In the device for producing a nanocluster liquid dispersion 300 according to the third embodiment, a nanocluster liquid dispersion is prepared by spraying the dispersion medium onto the surface of the substrate 51 on which nanoclusters are incident by the dispersion medium supply unit 53. Therefore, whenever nanoclusters are incident on the substrate 51, a new dispersion medium is supplied by spraying. Therefore, it is possible to prevent a cluster concentration in the liquid dispersion from increasing. Accordingly, it is possible to prepare a nanocluster liquid dispersion in which nanoclusters do not aggregate, but they are uniformly dispersed.

In the device for producing a nanocluster liquid dispersion 300 according to the third embodiment, when the nanocluster size generated in the nanocluster generation unit 10 is controlled, it is possible to isolate nanoclusters with a desired cluster size.

Method for Producing Nanocluster Liquid Dispersion

A method for producing a nanocluster liquid dispersion according to the present embodiment includes a nanocluster generation process in which nanoclusters are generated and a nanocluster collection process in which nanoclusters are collected in a dispersion medium while flowing on an incidence surface of the dispersion medium on which the generated nanoclusters are incident.

The nanocluster generation process is not particularly limited. The nanocluster generation process can be appropriately set according to a type and a cluster size of nanoclusters dispersed in the nanocluster liquid dispersion.

On the other hand, in the nanocluster generation process, it is preferable to control the cluster size. This is because the nanoclusters generated in the nanocluster generation process are collected in the nanocluster collection process. The nanocluster generation process in which the cluster size is controlled refers to a process in which a nanocluster with a cluster size showing a representative peak selected from a peak of a mass spectrum of the nanocluster generated in a gas phase is generated. A proportion of nanoclusters with a predetermined cluster size (showing a representative peak) with respect to all of the generated nanoclusters is preferably 5% or more.

Specifically, in the nanocluster generation process, the nanocluster generation device described in Patent Document 3 and the nanocluster generation unit in the above device for producing a nanocluster liquid dispersion can be used. The cluster size of the nanoclusters generated in the nanocluster generation process is controlled with an extremely high accuracy in a gas phase state. In the nanocluster generation process, when nanoclusters with a desired cluster size are generated in advance, the cluster size of the nanoclusters collected in a liquid dispersion collection process to be described below can be constant.

A type of the nanocluster generated in the nanocluster generation process is not particularly limited. Elements constituting the nanocluster may aggregate in a gas phase. Examples of the generated nanocluster include a metal nanocluster including a single metal element as a constituent element, an alloy nanocluster including a plurality of metal elements as constituent elements, and a semiconductor nanocluster including silicon as a constituent element. A nanocluster of Pt, Au, Ag, Cu, Cr, Ti, or Fe can be generated as the metal nanocluster, a nanocluster of CoPt, FePt, or the like can be generated as the alloy nanocluster, and Si, TaSi, TiSi, LuSi, RuSi, WSi, and MoSi can be generated as the semiconductor nanocluster.

Preferably, a nanocluster detection process is performed between the nanocluster generation process and the nanocluster collection process. In the nanocluster detection process, it is checked whether predetermined nanoclusters have been formed. As a result, it is possible to confirm that nanoclusters with a predetermined cluster size are included in the liquid dispersion and it is possible to increase a concentration of predetermined nanoclusters in the prepared nanocluster liquid dispersion.

In the nanocluster collection process, the dispersion medium on which nanoclusters are incident flows. This is because the nanoclusters generated in the nanocluster generation process are collected without aggregating.

For example, as in the above detection unit 30, when a probe plate is installed in the direction in which nanoclusters travel, the probe plate is colored in about several seconds. That is, nanoclusters are incident on the dispersion medium with a high frequency. Thus, when the dispersion medium does not flow, the nanoclusters that are incident on the dispersion medium aggregate with each other on the liquid surface or in the liquid. When the dispersion medium on which nanoclusters are incident flows, it is possible to prevent a nanocluster concentration from locally increasing on the surface of the dispersion medium and in the dispersion medium, and it is possible to increase dispersibility of the nanoclusters.

In the nanocluster collection process, on the surface of the liquid dispersion, nanoclusters are most likely to aggregate with each other. This is because, when nanoclusters are incident on the liquid surface, they receive resistance, and a speed of the nanoclusters temporarily decreases on the surface of the liquid dispersion.

Thus, in the nanocluster collection process, preferably, the dispersion medium flows so that a density of nanoclusters on the surface of the dispersion medium is equal to or less than an aggregation limit.

The aggregation limit refers to a density at which nanoclusters do not come in contact with each other on the surface of the dispersion medium. For example, if the nanocluster has a size of 1 nm in diameter, when there are $10^{14}$ nanoclusters or more in 1 $cm^2$, the nanoclusters come in contact with each other. Although the nanoclusters contacting with each other do not immediately aggregate, a density of nanoclusters on the surface of the dispersion medium is preferably $10^{14}$ nanoclusters/$cm^2$ or less for the nanocluster having a size of 1 nm in diameter.

The density of nanoclusters on the surface of the dispersion medium is greatly influenced also by a nanocluster incident flux. The incident flux refers to the number of particles of nanocluster that are incident in 1 $cm^2$ per second. When the incident flux is high, it is preferable to increase a flow velocity. When the incident flux is low, it is not as necessary to accelerate a stirring speed. In both cases, the dispersion medium flows so that the density of nanoclusters on the surface of the dispersion medium is an aggregation limit or less, and thus it is possible to further suppress aggregation of nanoclusters.

More specifically, for example, in order to collect 10 mg nanoclusters per hour, nanoclusters are incident on the liquid dispersion at 6 nmol (=$3.3\times10^{15}$ nanoclusters)/sec in an area of 12 $cm^2$ (calculated area of nanoclusters on the incidence surface at a diameter of 40 mm). An incident amount when the dispersion medium is fixed, $2.8\times10^{14}$ nanoclusters/sec.$cm^2$ is obtained. In this case, when a flow velocity is 10 cm/sec or more, the density of nanoclusters on the surface of the dispersion medium can be to $10^{14}$ nanoclusters/$cm^2$ or less. In consideration of a limit value of the current nanocluster incident flux, a surface speed of the nanocluster liquid dispersion is preferably 20 cm/sec or more and more preferably 100 cm/sec or more.

A method of flowing the dispersion medium on which nanoclusters are incident is not particularly limited. For example, the stirring bar, the rotating body, or the like described in the device for producing a nanocluster liquid dispersion can be used.

As described in the device for producing a nanocluster liquid dispersion, in principle, since the nanocluster liquid dispersion is prepared in the vacuum chamber, a solvent having low volatility with a high boiling point is preferably used. On the other hand, in consideration of the use mode, when a solvent having low volatility is used, the residual solvent is conceivable. Thus, the dispersion medium of the nanocluster liquid dispersion is preferably a volatile solvent.

Thus, a replacement process in which a dispersion medium is replaced with a volatile solvent having a lower boiling point than the dispersion medium used during collection may be additionally included after the nanocluster collection process. For replacement of the dispersion medium, first, only nanoclusters are extracted from the liquid dispersion according to, for example, column chromatography or a recrystallization method. Then, when the extracted nanoclusters are added to the volatile solvent again while stirring, a liquid dispersion in winch nanoclusters are dispersed in the volatile solvent is obtained. When the replacement process is performed in the presence of oxygen or water, there is a risk of nanoclusters aggregating. The replacement process is preferably performed under oxygen-free and anhydrous conditions using a glove box or the like. The solvent used for replacement is preferably subjected to a degassing and dehydration treatment.

When such a liquid dispersion is used, it is possible to easily apply the nanocluster liquid dispersion to the substrate. For coating, a spray coating method, a dispenser coating method, a spin coating method, a knife coating method, an inkjet coating method, a screen printing method, an offset printing method, or a die coating method can be used. When the solvent is removed from the applied liquid dispersion, a nanocluster dispersion film is easily obtained. A proportion of nanoclusters with a predetermined nanocluster size constituting the obtained nanocluster dispersion film with respect to all nanoclusters is 5% or more.

Here, the substrate is not particularly limited, and a conductive substrate, a non-conductive substrate, and the like are appropriately selected according to applications. Examples of the conductive substrate include a metal such as gold, silver, and aluminum, a metal oxide such as indium tin oxide (ITO), fluorine-doped tin oxide (FTO), and sapphire, and an organic conductor such as graphite and carbon nanotubes. In addition, examples of the non-conductive substrate include glass, a ceramic, and a resin. In addition, examples of the semiconductors include a semiconductor of Si, GaAs, and the like.

When the method for producing a nanocluster liquid dispersion according to the present embodiment is used, a nanocluster liquid dispersion in which nanoclusters are uniformly dispersed is obtained. In addition, in the nanocluster generation process, when the nanocluster size is controlled in advance, it is possible to isolate nanoclusters with a desired cluster size.

EXAMPLES

Hereinafter, effects of the present invention will become more apparent from examples. The present invention is not limited to the following examples, but can be appropriately changed and implemented within ranges in which the scope and spirit of the invention are not changed.

Example 1

First, nanocluster including Ta and Si as constituent elements in a gas phase were generated using the nanocluster generation unit described in the first embodiment.

Figure 7:
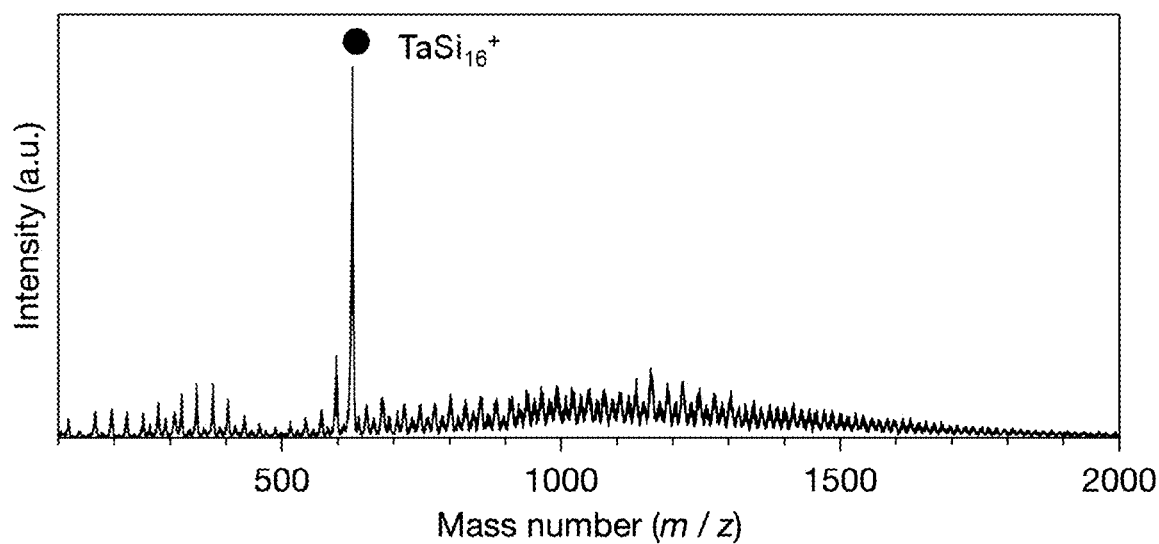
FIG. 7 is a mass spectrum of nanoclusters in a gas phase obtained when nanoclusters including Ta and Si as constituent elements were generated in a nanocluster generation unit.

FIG. 7 is a mass spectrum of nanoclusters generated in a gas phase. The nanoclusters generated in tire gas phase were confirmed as $TaSi_{16}^+$ from the mass spectrum.

Next, the nanoclusters generated in a gas phase were incident on the dispersion medium stored in the storage chamber to obtain a nanocluster liquid dispersion. As the dispersion medium, a polyethylene glycol dimethyl ether (PEG, molecular weight of about 250 u, boiling point 250° C. or more) having a methyl group as an inert substituent terminal was used. The dispersion medium was stirred by the stirring bar.

Figure 8:
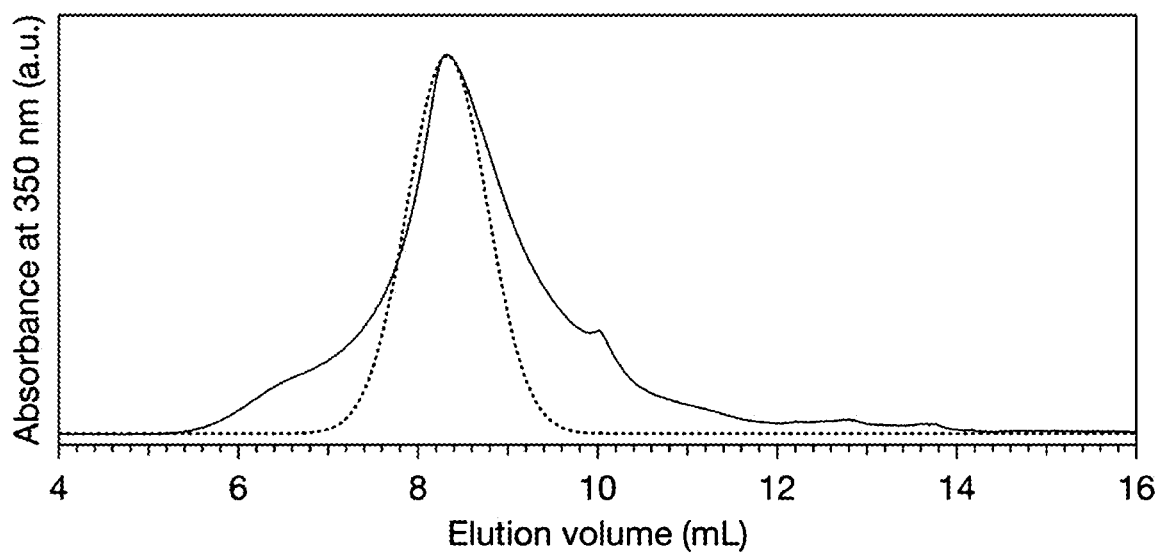
FIG. 8 is a high performance liquid chromatograph of a nanocluster liquid dispersion in which nanoclusters including Ta and Si as constituent elements were dispersed.

FIG. 8 is a high performance liquid chromatograph (HPLC) of a nanocluster liquid dispersion of TaSi. The horizontal axis represents an amount of a solution supplied to a column and the vertical axis represents an absorbance As the dispersion medium, a polyethylene glycol dimethyl ether (PEG, molecular weight of about 250 u, boiling point 250° C. or more) whose end was terminated with an inert methyl group was used and $TaSi_n^-$, $TaSi_n^+$, and $TaSi_n^{(0)}$ were generated as nanoclusters.

In the HPLC, while a solution was supplied from one side of an analysis column, an absorbance was measured using a spectrophotometer installed at the other side of the column. A size exclusion column was used for analysis. The analysis column had a porous structure therein, and a traveling speed in the analysis column differed according to the nanocluster size. Since nanoclusters with a small size traveled past the interior of the porous structure in the traveling direction, they had a lower traveling speed than nanoclusters with a large size. Therefore, nanoclusters with a relatively large size (large mass) were confirmed in a stage in which a volume of supplied solution into the analysis column was small. Subsequently, the nanocluster size decreased (small mass) as a volume of the solution supplied increased.

That is, the HPLC spectrum shown in FIG. 8 shows an abundance ratio of all nanoclusters included in the liquid dispersion. The horizontal axis represents an elution volume, that is, a cluster size, and the vertical axis represents an absorbance, that is, an abundance of clusters. Based on the graph, it was confirmed that there was a maximum peak at 8.5 mL (supply rate of a solvent at 0.5 mL/min, 17 minutes after the solvent was supplied) in the horizontal axis.

Figure 9A:
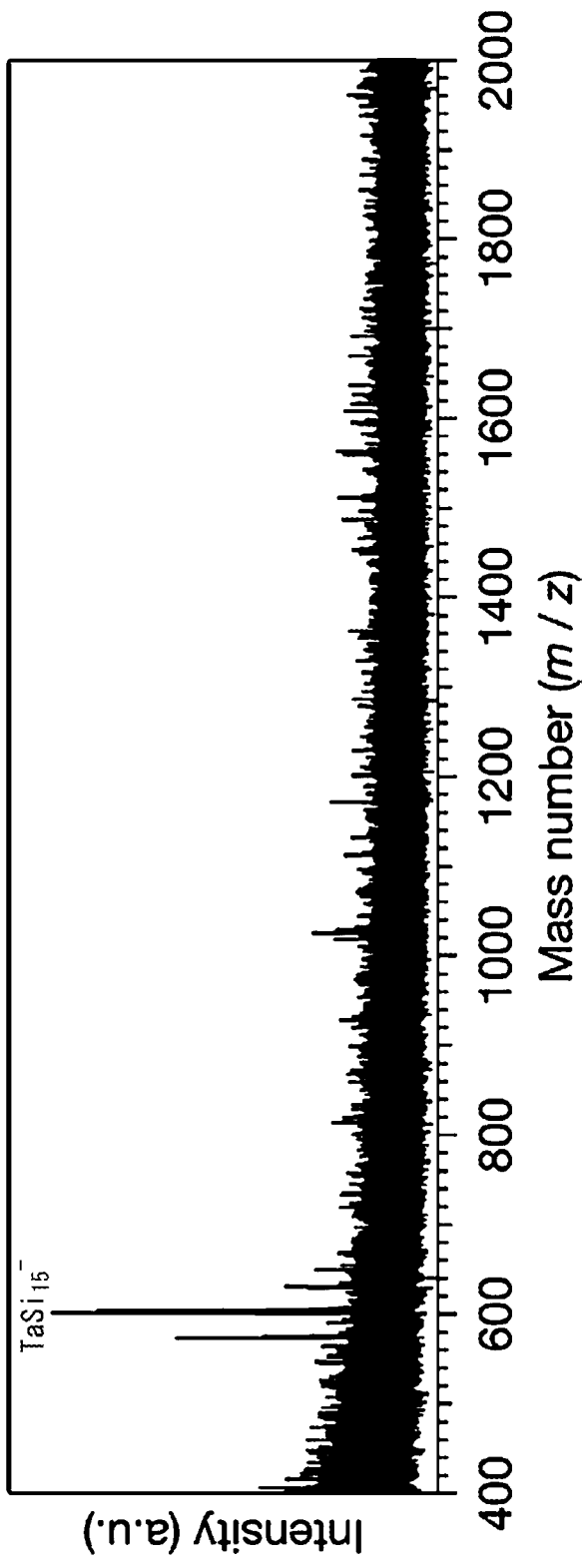
FIGS. 9A and 9B show negative ion mass spectra of a sample obtained by performing column purification on a nanocluster liquid dispersion prepared using a method for producing a nanocluster liquid dispersion according to an aspect of the present invention.
Figure 9B:
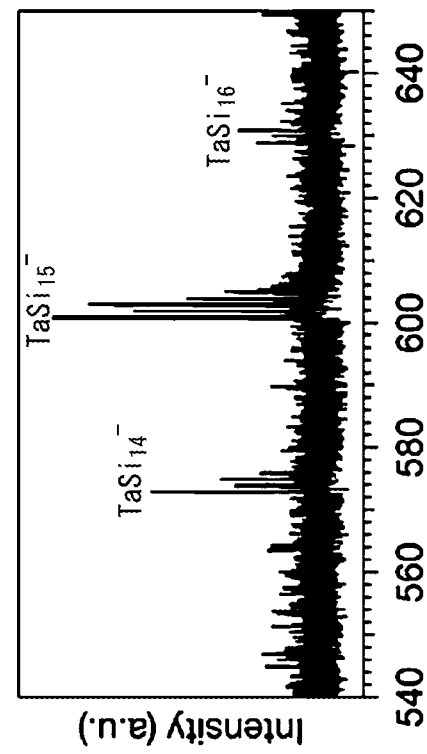

Next, a mass spectrum of a fraction component with respect to the representative peak of the nanocluster liquid dispersion was confirmed. FIGS. 9A and 9B show negative ion mass spectra of a sample obtained by performing column purification on a nanocluster liquid dispersion prepared using the method for producing a nanocluster liquid dispersion according to an aspect of the present invention, FIG. 9A shows the entire image of the mass spectrum, and FIG. 9B is an enlarged view in which the peak part is enlarged. The mass spectrum in FIGS. 9A and 9B was measured using the sample at a part of 8.5 mL in FIG. 8. The horizontal axis represents an m/z value obtained by dividing a mass number by a charge and the vertical axis represents a detection intensity.

As shown in FIGS. 9A and 9B, based on the result of mass analysis, it was found that $TaSi_{13}$-(m/z≅545 u), $TaSi_{14}$-(m/z ≅574 u), $TaSi_{15}$-(m/z≅602 u), and $TaSi_{16}$-(m/z≅630 u) were generated. These were assumed as fragmented products of $TaSi_{16}^+$. That is, a nanocluster showing the representative peak was $TaSi_{16}^+$ and it showed that $TaSi_{16}^+$ was included in the liquid dispersion as a main component. On the other hand, $Si_n^-$ with different sizes and different compositions were not observed. That is, in FIG. 7 and FIGS. 9A and 9B, it was confirmed that nanoclusters in a gas phase were dispersed in the dispersion medium without aggregating.

Next, a proportion of the confirmed nanoclusters with a predetermined cluster size ($TaSi_{16}^+$) with respect to all nanoclusters was calculated. The calculation was performed according to the following procedure.

First, the HPLC result obtained when a material of a single component (molecular weight was determined in one operation) was measured was confirmed.

Figure 10:
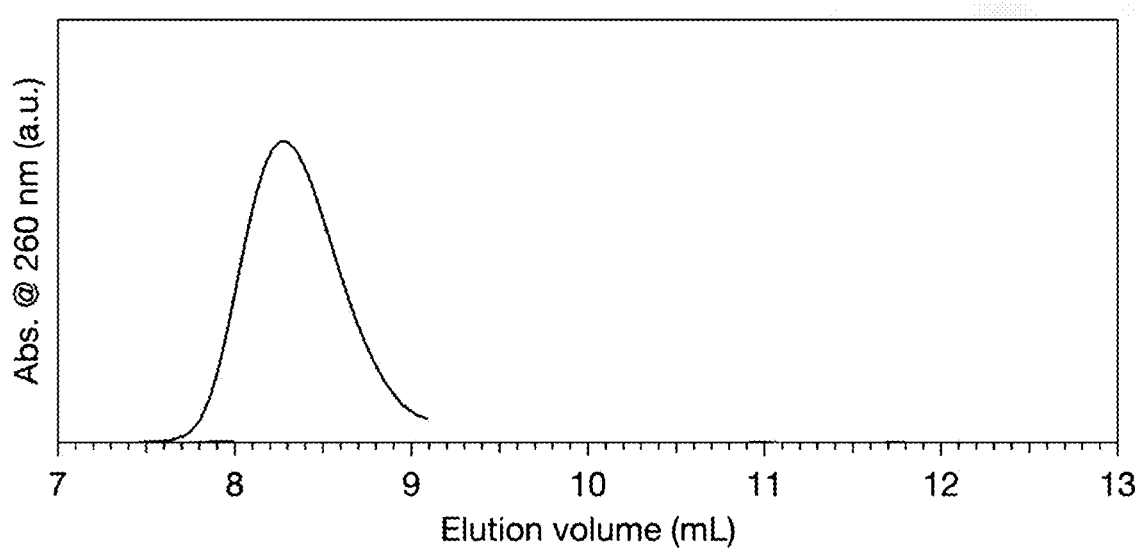
FIG. 10 is a high performance liquid chromatograph of a single component polystyrene.

FIG. 10 is an HPLC of a single component polystyrene. A half width of a peak obtained in this case was 0.63 mL and a peak value was 8.28 mL. The polystyrene having the same molecular weight was used as a reference material, and was detected as a peak curve with a certain width in the chromatogram.

That is, in the HPLC of the nanocluster liquid dispersion of TaSi shown in FIG. 8, a single $TaSi_{16}$ is detected as a peak curve with a certain width. Thus, the HPLC shown in FIG. 8 was fitted to a peak curve with a half width of 0.63 mL around a top point of the peak. A dotted line in FIG. 8 shows a fitting result. In other words, in the HPLC of the nanocluster liquid dispersion of TaSi, a dotted line part shows a peak generated due to $TaSi_{16}$. Thus, an area proportion of the dotted line part with respect to the area of the solid line part can be converted into a proportion of the confirmed nanoclusters with a predetermined cluster size ($TaSi_{16}^+$) with respect to all nanoclusters.

As the result obtained by conversion in the above procedure, a proportion of the confirmed nanoclusters with a predetermined cluster size ($TaSi_{16}^+$) with respect to all nanoclusters was 57.2%.

As described above, a nanocluster liquid dispersion in which nanoclusters including TaSi as a constituent element were dispersed was obtained. In addition, the obtained nanocluster liquid dispersion was stable and precipitation of nanoclusters was not observed after the liquid dispersion was left for about 6 months. That is, it was found that nanoclusters with a predetermined size were uniformly dispersed in the nanocluster liquid dispersion.

Example 2

The PEG liquid dispersion of the TaSi nanoclusters prepared in Example 1 was recrystallized using a hexane/acetonitrile mixture solvent and the TaSi nanoclusters were separated from the dispersion medium. The separated TaSi nanoclusters were dispersed in tetrahydrofuran, and toluene again. In both cases, the TaSi nanoclusters after re-dispersion were not precipitated, but they were stably dispersed. It was confirmed that the dispersion medium could be replaced with a volatile organic solvent with a high volatility from a PEG with a low volatility. In addition, the liquid dispersion after replacement was stable and precipitation of the nanoclusters was not observed.

Example 3

Example 3 was the same as Example 1 except that elements constituting nanoclusters generated in a gas phase in the nanocluster generation unit were Ti and Si. The obtained nanocluster was $TiSi_n$.

Figure 11:
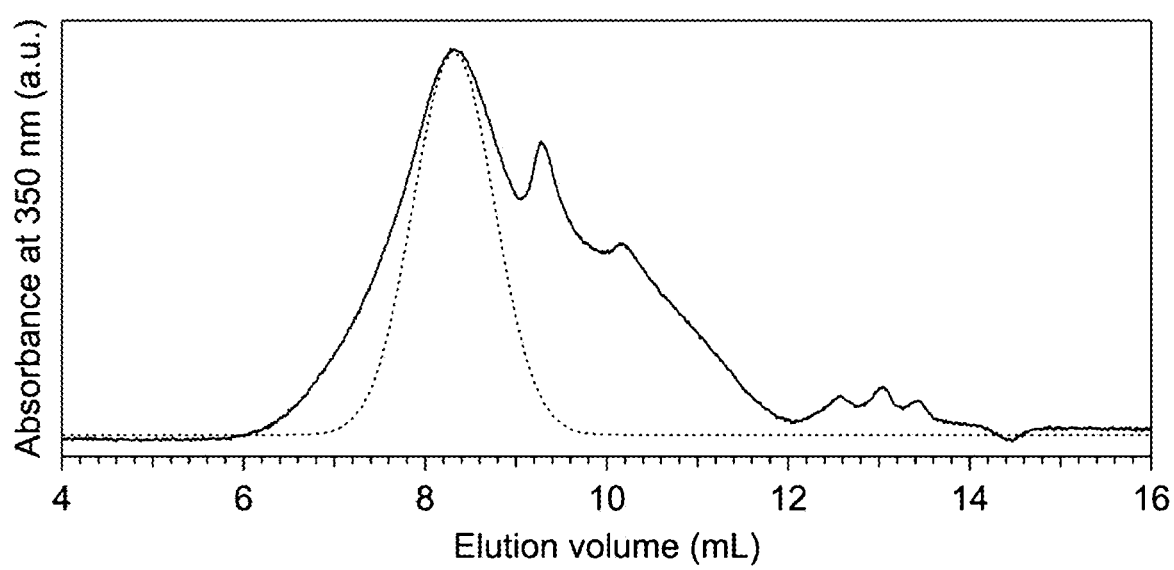
FIG. 11 is a high performance liquid chromatograph of a nanocluster liquid dispersion in which nanoclusters including Ti and Si as constituent elements are dispersed.

FIG. 11 is an HPLC of a nanocluster liquid dispersion of TiSi prepared using the method for producing a nanocluster liquid dispersion according to an aspect of the present invention. The solid line shows HPLC results of all nanoclusters, and the dotted line shows a distribution of nanoclusters with a cluster size in the process confirmed through fitting.

In the same procedure as in Example 1, a calculated proportion of nanoclusters with a predetermined cluster size with respect to all nanoclusters was 40.2%. In addition, the obtained nanocluster liquid dispersion was stable and precipitation of nanoclusters was not observed after the liquid dispersion was left for about 6 months.

Example 4

The PEG liquid dispersion of the TiSi nanoclusters prepared in Example 3 was recrystallized using a hexane/acetonitrile mixture solvent. Then, the TiSi nanoclusters were separated from the dispersion medium. The TiSi nanocluster sample separated from the dispersion medium included Si at 15 weight % or more and Ti at 1 weight % or more, and the remaining component that was polyethylene glycol dimethyl ether bonded to the nanocluster. The TiSi nanoclusters separated from the dispersion medium were dispersed in tetrahydrofuran again. The TiSi nanoclusters after re-dispersion were not precipitated and were stably dispersed. It was confirmed that the dispersion medium could be replaced with a volatile organic solvent with a high volatility from a PEG with a low volatility. In addition, the liquid dispersion after replacement was stable and precipitation of the nanoclusters was not observed.

Example 5

Example 5 was the same as Example 1 except that elements constituting nanoclusters generated in a gas phase in the nanocluster generation unit were Ru and Si. The obtained nanocluster was $RuSi_n^+$.

Figure 12:
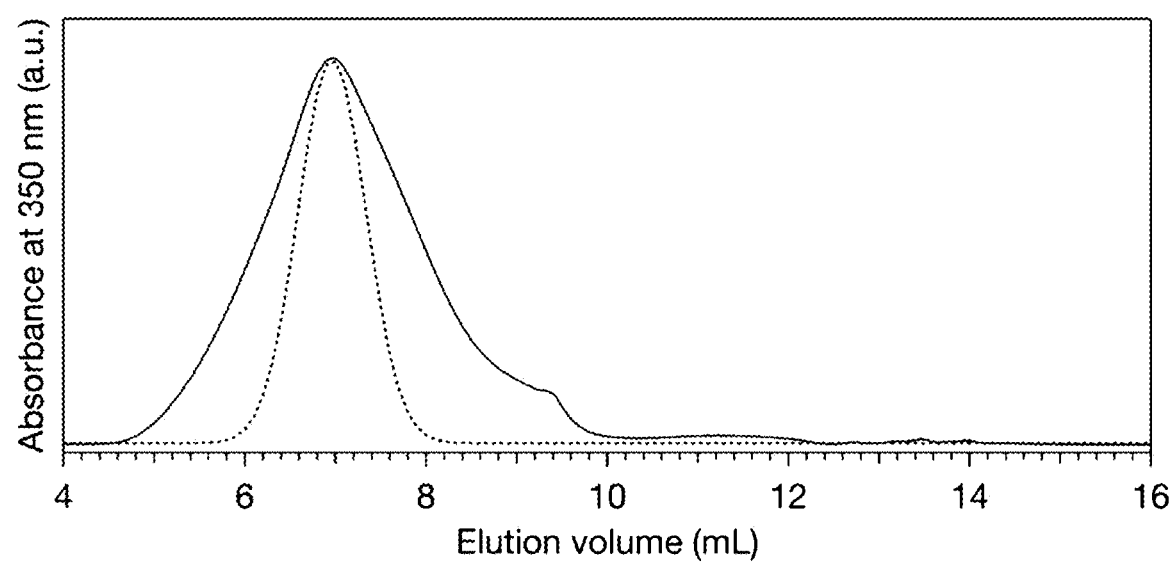
FIG. 12 is a high performance liquid chromatograph of a nanocluster liquid dispersion in which nanoclusters including Ru and Si as constituent elements are dispersed.

FIG. 12 is an HPLC of a nanocluster liquid dispersion of RuSi prepared using the method for producing a nanocluster liquid dispersion according to an aspect of the present invention. The solid line shows HPLC results of all nanoclusters, and the dotted line shows a distribution of nanoclusters with a cluster size in the process confirmed through fitting.

In the same procedure as in Example 1, a calculated proportion of nanoclusters with a predetermined cluster size with respect to all nanoclusters was 42.1%. In addition, the obtained nanocluster liquid dispersion was stable and precipitation of nanoclusters was not observed after the liquid dispersion was left for about 3 months.

Examples 6 and 7

TaSi and TiSi nanocluster liquid dispersions that were dispersed in tetrahydrofuran again, which were obtained in Example 2 and Example 4, were applied to a glass substrate and a Si substrate. More specifically, a solution of 10 mg/mL was applied to a Si substrate with an oxide film (111) using a spin coater (device: model number SC2005 commercially available from Aiden) at a rotational speed of 3000 rpm. The coated sample was dried by air to prepare a TaSi nanocluster dispersion film. FIG. 14 is a cross-sectional view of the nanocluster dispersion film.

Example 8 to 10

TiSi nanocluster liquid dispersions were prepared in the same method as in Example 4 except that, as a hardly volatile dispersion medium used when a nanocluster liquid dispersion was prepared, a dimethyl silicone oil (Example 7, viscosity 200 mm²/s), a dimethyl silicone oil (Example 8, viscosity 1000 mm²/s) and a methylphenyl silicone oil (Example 9, viscosity 160 mm²/s) were used in place of the polyethylene glycol dimethyl ether. In addition, the obtained nanocluster liquid dispersion was stable and precipitation of nanoclusters was not observed after the liquid dispersion was left for about 6 months. Precipitation of the nanoclusters was visually evaluated.

Examples 11 and 12

An ionic liquid was used as a hardly volatile dispersion medium used when a nanocluster liquid dispersion was prepared. As the ionic liquid, 1-butyl-3-methylimidazolium hexafluorophosphate was used in Example 11 and 1-butyl-1-methylpyrrolidinium bis(trifluoromethanesulfonyl)imide was used in Example 12. When the TiSi nanocluster liquid dispersion was prepared using such anionic liquid and left for 1 week, slight association between the nanoclusters was observed. Compared to the nanocluster liquid dispersions prepared in Examples 1 to 5 and 8 to 10, dispersibility was not favorable.

Example 13

A TiSi nanocluster liquid dispersion was prepared using a liquid paraffin as a hardly volatile dispersion medium used when a nanocluster liquid dispersion was prepared. When the prepared nanocluster liquid dispersion was left for 1 week, slight association between the nanoclusters was observed. Compared to the nanocluster liquid dispersions prepared in Examples 1 to 5 and 8 to 10, dispersibility was not favorable.

REFERENCE SIGNS LIST

100 Device for producing nanocluster liquid dispersion
10 Nanocluster generation unit
11, 44, 56 Vacuum chambers
12 Nanocluster growth cell
13 Sputtering source
14 Liquid nitrogen jacket
15 Control device
16 Pulse power supply
17 First inert gas introduction unit
18 Second inert gas introduction unit
19, 47, 57 Exhaust device
20, 40, 50 Nanocluster collection unit
21, 41 Storage chamber
22 Stirring bar
23, 43 Dispersion medium
30 Detection unit
42 Rotating body
45, 55 Petcock
46 Support
48 Squeegee
49 Stirring unit
51 Substrate
52 Cooling unit
53 Dispersion medium supply unit
54 Collection container

The invention claimed is:

1. A method for producing a nanocluster liquid dispersion, the method comprising:
generating nanoclusters, thereby forming generated nanoclusters; and
collecting the nanoclusters in a dispersion medium that is flowing in a direction in which the nanoclusters travel, wherein the nanoclusters are in contact with the dispersion medium, and wherein at least a part of the dispersion medium flows along and follows an outer surface of a rotating body.

2. The method according to claim 1,
wherein, the dispersion medium flows so that a density of nanoclusters on a surface of the dispersion medium does not exceed an aggregation limit, in the collecting.

3. The method according to claim 1,
wherein the dispersion medium is a solvent having low volatility with a boiling point of 160° C. or more and a vapor pressure of 100 Pa or less at room temperature.

4. The method according to claim 1, further comprising after the collecting:

replacing the dispersion medium with a volatile dispersion medium having a boiling point lower than a boiling point of the dispersion medium.

5. The method according to claim 1, further comprising between the generating and the collecting:

detecting whether predetermined nanoclusters are generated in the generating.

6. The method according to claim 1, wherein the dispersion medium has an ether bond or a siloxane bond, and wherein an end of the ether bond or the siloxane bond has an inert substituent terminal.

* * * * *